(12) United States Patent
Westlund et al.

(10) Patent No.: US 8,155,760 B2
(45) Date of Patent: Apr. 10, 2012

(54) MEDICAL LEAD SYSTEM UTILIZING ELECTROMAGNETIC BANDSTOP FILTERS

(75) Inventors: Randy Westlund, River Falls, WI (US); Robert A. Stevenson, Canyon Country, CA (US); Christine A. Frysz, Orchard Park, NY (US); Warren S. Dabney, Orchard Park, NY (US); Henry R. Halperin, Pikesville, MD (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/026,949

(22) Filed: Feb. 14, 2011

(65) Prior Publication Data
US 2011/0144734 A1 Jun. 16, 2011

Related U.S. Application Data

(63) Continuation-in-part of application No. 11/943,883, filed on Nov. 21, 2007, now Pat. No. 7,899,551, which is a continuation-in-part of application No. 11/558,349, filed on Nov. 9, 2006, now Pat. No. 7,945,322, which is a continuation-in-part of application No. 11/423,073, filed on Jun. 8, 2006, which is a continuation-in-part of application No. 10/123,534, filed on Apr. 15, 2002, now Pat. No. 7,844,319.

(60) Provisional application No. 60/283,725, filed on Apr. 13, 2001, provisional application No. 60/803,672, filed on Jun. 1, 2006, provisional application No. 60/597,125, filed on Nov. 11, 2005.

(51) Int. Cl.
*A61N 1/00* (2006.01)
(52) U.S. Cl. ...................................................... 607/122
(58) Field of Classification Search .................. 607/122
See application file for complete search history.

(56) References Cited

U.S. PATENT DOCUMENTS

| 5,209,233 | A | 5/1993 | Holland et al. |
| 6,529,000 | B2 * | 3/2003 | Lou ............................ 324/309 |
| 7,363,090 | B2 | 4/2008 | Halperin |
| 7,702,387 | B2 | 4/2010 | Stevenson |
| 7,853,325 | B2 | 12/2010 | Dabney |
| 2007/0112398 | A1 | 5/2007 | Stevenson |
| 2008/0049376 | A1 | 2/2008 | Stevenson |
| 2008/0132987 | A1 | 6/2008 | Westlund |
| 2008/0195180 | A1 | 8/2008 | Stevenson |
| 2008/0269591 | A1 | 10/2008 | Halperin |
| 2010/0100164 | A1 | 4/2010 | Johnson |
| 2010/0198312 | A1 | 8/2010 | Stevenson |
| 2010/0280584 | A1 | 11/2010 | Johnson |
| 2010/0324640 | A1 | 12/2010 | Bauer |

* cited by examiner

*Primary Examiner* — George Manuel
(74) *Attorney, Agent, or Firm* — Michael F. Scalise; Kelly & Kelley LLP

(57) ABSTRACT

Medical lead systems utilizing electromagnetic bandstop filters are provide which can be utilized in a magnetic resonance imaging (MRI) environment for patients who have implanted medical devices. The medical lead system includes an implanted lead having at least one bandstop filter associated therewith, for attenuating current flow through the lead over a range of frequencies. The bandstop filter has an overall circuit Q wherein the resultant 3 dB bandwidth is at least 10 kHz. The values of capacitance and inductance of the bandstop filter are selected such that the bandstop filter is resonant at a selected center frequency. Preferably, the bandstop filter has an overall circuit Q wherein the resultant 10 dB bandwidth is at least 10 kHz. Such bandstop filters are backwards compatible with known implantable deployment systems and extraction systems.

21 Claims, 21 Drawing Sheets

| French Guage | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |
| 13 | 4.3 | 0.170 |
| 14 | 4.7 | 0.184 |
| 15 | 5 | 0.197 |
| 16 | 5.3 | 0.210 |
| 17 | 5.7 | 0.223 |
| 18 | 6 | 0.236 |
| 19 | 6.3 | 0.249 |
| 20 | 6.7 | 0.263 |
| 22 | 7.3 | 0.288 |
| 24 | 8 | 0.315 |
| 26 | 8.7 | 0.341 |
| 28 | 9.3 | 0.367 |
| 30 | 10 | 0.393 |
| 32 | 10.7 | 0.419 |
| 34 | 11.3 | 0.455 |

FIG.1A

| French Guage | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |
| 13 | 4.3 | 0.170 |
| 14 | 4.7 | 0.184 |
| 15 | 5 | 0.197 |
| 16 | 5.3 | 0.210 |
| 17 | 5.7 | 0.223 |
| 18 | 6 | 0.236 |
| 19 | 6.3 | 0.249 |
| 20 | 6.7 | 0.263 |
| 22 | 7.3 | 0.288 |
| 24 | 8 | 0.315 |
| 26 | 8.7 | 0.341 |
| 28 | 9.3 | 0.367 |
| 30 | 10 | 0.393 |
| 32 | 10.7 | 0.419 |
| 34 | 11.3 | 0.455 |

MEDICAL LEAD SYSTEM UTILIZING ELECTROMAGNETIC BANDSTOP FILTERS

FIELD OF THE INVENTION

The present invention relates to medical lead systems adapted for use in a magnetic resonant imaging (MRI) environment for patients who have implanted medical devices. More particularly, the present invention relates to such medical lead systems which incorporate electromagnetic bandstop filters.

BACKGROUND OF INVENTION

Magnetic resonance imaging (MRI) is currently contraindicated for patients who have implanted medical leads. This is due largely to the patient safety issue that results when the strong electromagnetic fields of an MRI system interact with the antenna-like therapy delivery leads of an active implantable medical device (AIMD). It is well documented that the radio frequency (RF) signals that are generated by the MRI system can couple along the length of a lead conductor or conductors and create induced RF currents. These RF currents can cause significant heating at points of high current concentration, the most significant of which is at the distal tip electrode, where the lead system makes direct contact with body tissue. Excessive RF currents at the point of electrode contact to tissue can create a serious or even life-threatening situation. In the literature, there are reports of MRI induced thermal damage to brain tissue from around the area of implanted deep brain stimulation electrodes, pacemaker pacing capture threshold changes or even loss of capture which means that a pacemaker dependent patient is without life support.

AIMDs can include completely implantable systems or a combination of externally worn devices with implanted leads. AIMDs include the group of cochlear implants, piezoelectric sound bridge transducers and the like. AIMDs can also include a variety of neurostimulators and brain stimulators. Sometimes these are called neuromodulators. Neurostimulators are used to stimulate the vagus nerve, for example, to relieve epilepsy, obesity, and depression. Deep brain stimulators are pacemaker—like devices and include electrodes implanted deep into the brain matter for sensing the onset of the seizure and also providing electrical stimulation to brain tissue to prevent the seizure from actually occurring. There are also other types of deep brain stimulators used to correct other abnormalities, such as Tourette's Syndrome and the like. AIMDs also include all types of cardiac pacemakers, left ventricular assist devices (LVADs), artificial hearts and implantable cardioverter defibrillators. AIMDs also include drug pumps which can be used for dispensing of insulin, chemotherapy drugs, pain medications and the like. AIMDs can include a variety of implanted or external-implanted bone growth stimulators for rapid healing of fractures. AIMDs may also include urinary incontinence devices, pain release spinal cord stimulators, anti-tremor stimulators, congestive heart failure devices, cardiac resynchronization therapy devices (CRT), and the like.

As disclosed in US 2007/0112398 A1 and U.S. Pat. No. 7,853,325, the contents of which are incorporated herein by reference, a novel method to n minimize the expected heating at the distal tip of the lead system is to incorporate a bandstop filter. This bandstop filter is comprised of an inductor and capacitor in parallel, with the bandstop filter connected in series with one or more conductors of the implanted lead system. In such a system, the bandstop filter is constructed so that its resonant frequency or frequencies coincides with the RF operating frequency of one or more MRI systems.

RF frequencies are directly related to the MRI machine static magnetic field by the Lamour Relationship wherein the frequency is equal to 42.56 times the static field strength in Teslas (for hydrogen scanners). Typical MRI RF pulsed frequencies are 64 MHz for 1.5 T systems and 128 MHz for 3.0 T systems. At resonance, the impedance of the bandstop filter is quite high (for example, above 2,000 ohms) which reduces the flow of distal electrode to tissue current at the MRI RF pulsed frequency thereby reducing implanted lead and/or electrode heating. Increasing the impedance at the lead distal tip electrode greatly reduces the amount of RF current that would flow into body tissue. It has been documented that excess current can cause tissue damage, pacing capture threshold (PCT) changes or even tissue necrosis.

Implementation of this technology in implantable leads is a significant challenge. Bandstop filters for use in implantable lead systems must be biocompatible, not significantly change the electrical performance characteristics of the lead (except within the context of the invention), and must not significantly affect size, weight, or implantability. With increasingly smaller leads being developed to accommodate small vasculature and left ventricular pacing through the coronary sinus, bandstop technology must be equally scalable to match the same demands.

The present invention satisfies these needs and provides other related advantages.

SUMMARY OF THE INVENTION

The present invention relates to medical lead systems which utilize electromagnetic bandstop filters. Such medical lead systems are advantageously utilized in a magnetic resonance imaging (MRI) environment for patients who have implanted medical devices.

The medical implantable lead system of the present invention may include a lead body configured for insertion into a venous system. The implantable lead may include a terminal pin (such as an ISO IS-1) at one end for connecting the lead system to the active implantable medical device (AIMD). An electrode is provided at the distal end which is in contact with biological cells. The bandstop filter associated with the lead attenuates current flow through the lead at a selected frequency or range of frequencies.

In a preferred form of the invention, the medical lead system comprises an implantable lead having a proximal end and an electrode in contact with biological cells at a distal end. At least one bandstop filter is associated with the lead for attenuating current flow through the lead over a range of frequencies. The bandstop filter has an overall circuit Q wherein the resultant 3 dB bandwidth is at least 10 kHz. The bandstop filter comprises a capacitor in parallel with an inductor, said parallel capacitor and inductor being placed in series with the lead wherein values of capacitance and inductance are selected such that the bandstop filter is resonant at a selected center frequency.

In a particularly preferred form, the range of frequencies comprises a plurality of MRI RF pulsed frequencies. Moreover, the bandstop filter is designed to have an overall circuit Q wherein the resultant 10 dB bandwidth is at least, in some embodiments, 10 kHz, in others at least 100 kHz, and in still others at least 0.5 MHz In an illustrated embodiment, the lead comprises a proximal section and a reduced-diameter lead extension, wherein the bandstop filter is disposed between the proximal section and the lead extension. The bandstop filter may include optional fixation tines. The physical length of the lead extension is preferably less than ½ of the electrical wavelength of the selected center frequency, and in some cases is designed to be less than ¼ or ⅛ of the electrical wavelength of the selected center frequency. Preferably, the lead extension beyond the bandstop filter is less than 15 cm.

The lead may comprise an epicardial lead, a split-cylinder cup electrode, a self-sizing nerve cuff, a multiple-cup nerve electrode, a multiple bandstop filter array, a deep brain electrode, a paddle electrode, a PAD electrode, a ring electrode, an active fixation tip electrode, a passive fixation tip electrode, a lead extension electrode, or an ablation probe. The bandstop filter may be incorporated into any of these components. In the multiple bandstop filter array, a plurality of bandstop filters may be disposed on a substrate, along the implanted lead, or in a PAD or paddle electrode array. In this instance, at least one of the bandstop filters may comprise a bandstop filter chip, or at least one of the bandstop filters may be thick-film deposited onto the substrate.

A deep brain probe/housing with one or more bandstop filters may be disposed either flush with the skull, recessed, or subdural with a lead extension implanted into brain tissue. A flexible conductor may be disposed between the bandstop filter and the electrode lead extension.

The ring electrode may comprise a cochlear electrode.

In all of these instances, the bandstop filter may be disposed within or adjacent to the electrode, or at the proximal end of a lead extension.

Other features and advantages of the present invention will become apparent from the following more detailed description, taken in connection with the accompanying drawings which illustrate, by way of example, the principles of the invention.

BRIEF DESCRIPTION OF THE DRAWINGS

FIG. 1A is a table showing the relationship between French sizes and millimeters and inches.

DETAILED DESCRIPTION OF THE PREFERRED EMBODIMENTS

The present invention is directed to medical lead systems comprising an implanted lead having a proximal end and an electrode in contact with biological cells at a distal end. At least one bandstop filter is associated with the lead for attenuating current flow through the lead over a range of frequencies. The bandstop filter has an overall circuit Q wherein the resultant 3 dB bandwidth is at least 10 kHz and where the bandstop filter comprises a capacitor in parallel with an inductor. The parallel capacitor and inductor are placed in series with the lead wherein values of capacitance and inductance are selected such that the bandstop filter is resonant at a selected center frequency. As used herein, the term bandwidth refers to an attenuation or insertion loss plot of the bandstop filter performance versus frequency. At its resonant center frequency, the bandstop filter has an attenuation peak. The bandwidth is the difference in frequency either computed 3 dB or 10 dB down from the peak.

Figure 1:
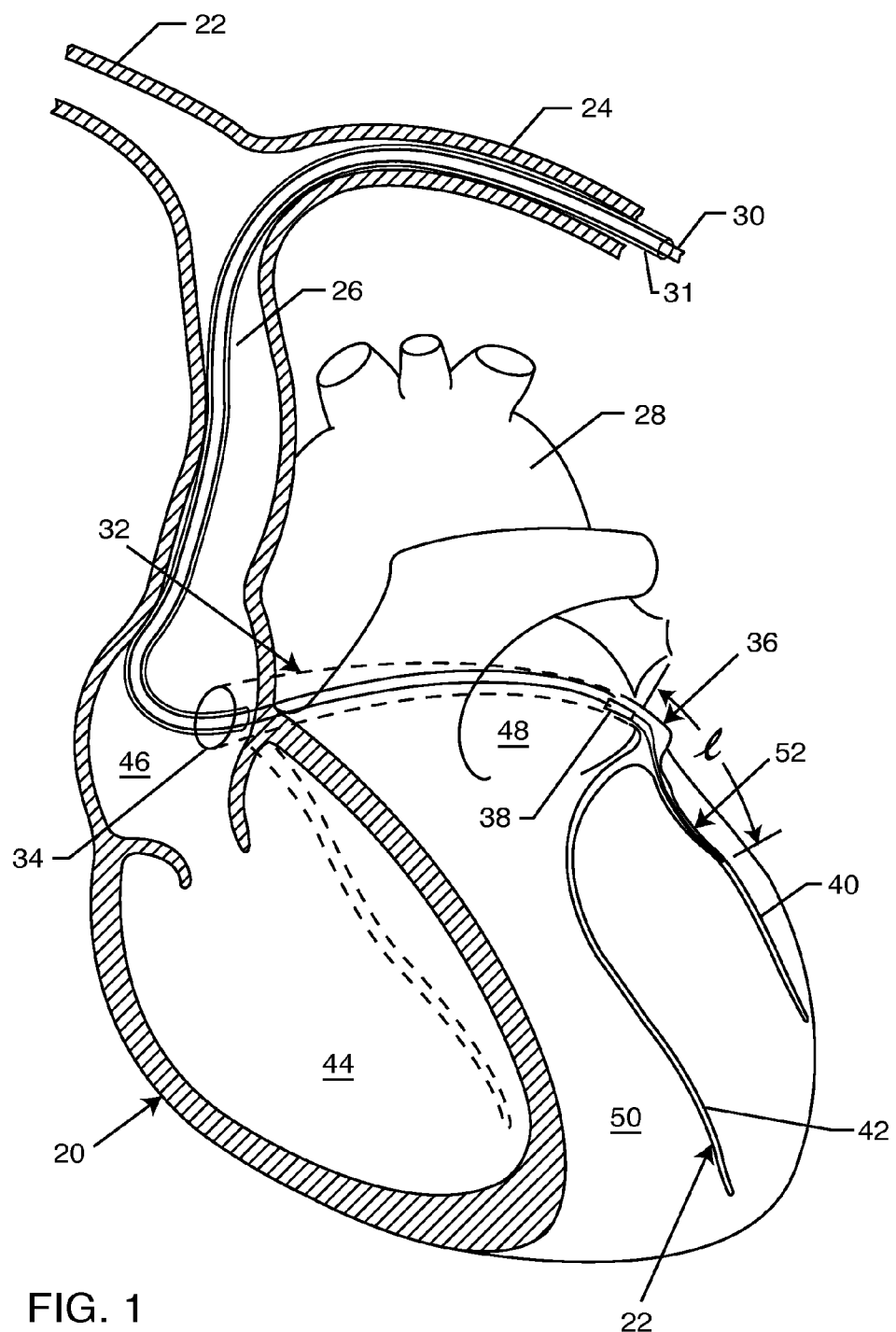
FIG. 1 is a diagrammatic representation of the human heart, showing a left ventricular endocardial lead system embodying the present invention.

FIG. 1 is a diagrammatic representation of a human heart 20 which includes right and left subclavian veins 22 and 24 respectively, the superior vena cava 26 and the aorta 28. A lead 30, which is typically routed from a biventricular cardiac pacemaker or a biventricular implantable cardioverter defibrillator (ICD) (which are not shown), is routed through a catheter 31 and directed, in this case, through the left subclavian vein 24 and then down through the superior vena cava 26 and into the coronary sinus 32. The lead 30 must first enter the coronary sinus ostium 34 where the implanting physician selects the correct location. The coronary sinus 32 is actually divided into two zones: the first part (on the left) is known as the coronary sinus 32; and the second part (on the right) is called the great cardiac vein 36. The great cardiac vein 36 wraps around the back of the left ventricle. The bandstop filter 38 is intended to be placed ideally near the end of the great cardiac vein 36 where it breaks into several venous branches. These branches are called the posterior branch, the lateral branch 40 and the anterior branch 42. A more comprehensive name, for example, would be the interventricular branch.

Again referring to FIG. 1, one can also see the right ventricle 44 and the right atrium 46. Also shown are the left atrium 48 and the left ventricle 50. The ideal location for a bandstop filter 38 is shown. An ideal length for the bandstop filter 38 would be between 5 and 7.5 mm in length. At this particular location, at the end of the great cardiac vein 36, cardiac motion is relatively small and fibrotic tissue will tend to encapsulate the bandstop filter 38 and its associated lead 30 and thereby attach it/fixate it in position in this relatively low motion region. This is particularly advantageous in that the lead 30 will remain highly reliable and resistant to breakage. Because of the relatively large diameter of the coronary sinus 32 and the great cardiac vein 36, this portion of the lead system, including the bandstop filter 38, can be of much larger diameter (for example, 7 or 8 French). Beyond this point, where the great cardiac vein 36 branches, the venous systems become much smaller. In general, these branches are below 6 French in diameter and ideal electrode sizes go all the way down to 3 French.

FIG. 1A shows the relationship between French size, millimeters and inches. Since left ventricular pacing is important for cardiac resynchronization and treatment of congestive heart failure, it is a feature of the present invention that a lead body diameter/size reduction occurs at distal end of the bandstop filter 38 allowing insertion of the smaller diameter/size lead extension 52 with distal electrodes into the small diameter venous system in the proper position outside the left ventricle 50.

The primary benefit of locating the bandstop filter 38 in the coronary sinus 32 and/or great cardiac vein 36 is that the diameter of the bandstop filter 38 itself can be larger making it much easier to manufacture. The distal portion 52 of the lead 30 from the bandstop filter 38 is smaller (3 to 6 French size) for easier employment and navigation into the branch veins of the left ventricle 50. Secondary benefits beyond the diameter of the bandstop filter 38 include the length of the bandstop filter. Entering into and navigating the coronary sinus 32 and great cardiac vein 36 generally involve larger bend radii compared to accessing and navigating the branch vessels. Therefore the lead extension 52 that traverses through and resides in the branch vessels must be very small and very flexible, not having a stiff section longer than approximately 1.5 mm as a rule of thumb. Rigid sections of the lead 30 measuring longer than 1.5 mm can impede the ability to navigate around the tight corners and bends of the branch vessels. In the coronary sinus 32 and great cardiac vein 36, however, there is substantially more latitude, and stiff sections of the lead could approach 5 mm or even 7.5 mm without drastically impeding deliverability.

A secondary benefit of locating the bandstop filter 38 in the coronary sinus 32 or the great cardiac vein 36 has to do with MRI image artifacts. Although the image artifact will be quite small due to avoiding the use of ferromagnetic materials, it is still beneficial to locate the bandstop filter 38 away from the coronary arteries, ventricular wall motion or other anatomies/physiologies/pathologies of most interest. If a bandstop filter 38 is located in the coronary sinus 32, however, it could generate small artifact in the vicinity of the valves. Another benefit of having the bandstop filter 38 located in the coronary sinus 32 or the great cardiac vein 36 is that its rigidity provides a foundation on which optional fixation fixtures may be more strategically utilized. For example, one or more tines could originate from the region of the lead where the bandstop filter 38 resides. Additionally, rigidity of the bandstop filter 38 makes the tines more effective in their engagement of the vessel walls. Alternatively, a rigid portion of the lead 30, skillfully navigated beyond a corner or bifurcation, can function as a fixation mechanism that proves difficult or requires skill to track the lead.

The portion of an implanted lead 30 which is distal of a bandstop filter is known as the lead extension 52. In general, this lead extension 52 at its proximal end will be connected to the bandstop filter 38 and its distal end will terminate in electrodes in contact with body cells or tissue. For the purposes herein, it is important that the electrical wave length ($\lambda$) of the lead extension 52 not be physically too long. This has to with its efficiency as an antenna and picking up energy from the RF pulsed fields of an MRI system. In general, for 1.5 Tesla systems, lead lengths that couple very efficiently are in the 42 to 60 cm range. In a preferred embodiment, the length ($\lambda$) of any lead extension, whether it be for a cardiac application, a deep brain application or the like, should be less than ⅛ of an electrical wavelength (⅛$\lambda$). It has been shown that leads that are less than ⅛ of electrical wavelength of the MRI RF frequency do not act as effective antennas and therefore pick up an insignificant amount of energy from the external MRI RF pulse field. In some cases, the electrical length of the lead extension could be as long as ¼ or even ½$\lambda$. In these cases, variables include the lead trajectory, the sensitivity of the tissues that are in contact with a distal electrode, patient characteristics and the like. For example, myocardial tissue is much less subject to thermal damage than is deep brain tissue.

Figures 2, 2A:
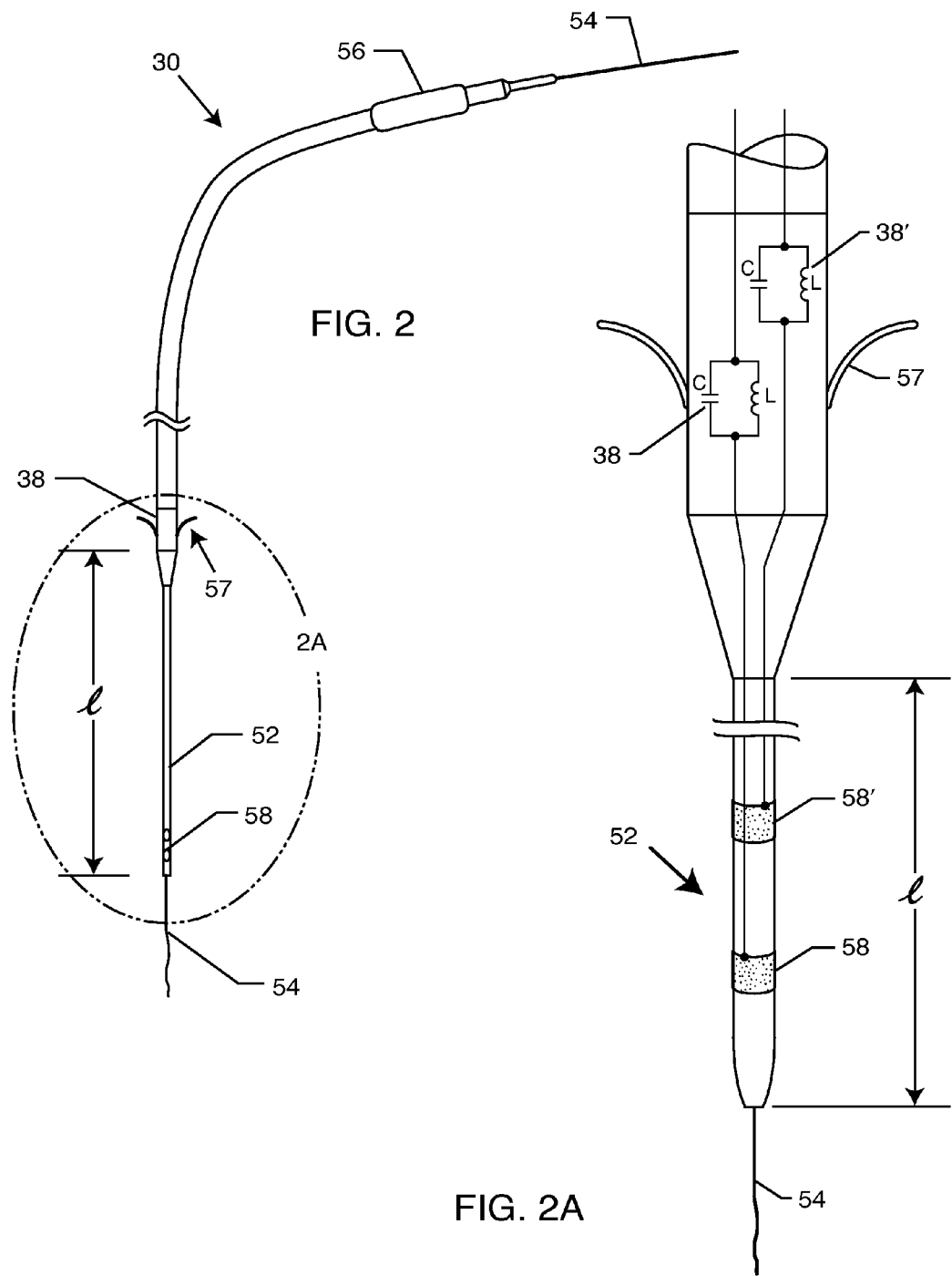
FIG. 2 is an enlarged perspective view of the lead system of FIG. 1.
FIG. 2A is an enlarged view of the distal lead taken generally of the area indicated by the line 2A in FIG. 2.

FIG. 2 is an enlarged perspective view of the lead system 30 taken from FIG. 1. One can see that there is a guide wire 54 which is common in the prior art for inserting into position prior to sliding the highly flexible lead system 30 down over it. A terminal pin 56 is designed to plug into an implantable medical device, such as a pacemaker or ICD. The bandstop filter 38 is shown at the point where the lead 30 would be reduced from 6-9 French down to the 3-6 French lead extension 52. Optional fixation tines 57 are shown which may be affixed, disposed, or adjacent to the bandstop filter 38. By way of reference, the French scale is related to both diameter in millimeters (mm) or inches. For example, 7 French is 23 mm (0.092 inch) in diameter and 3 French is only 1 mm in diameter (0.039 inch). The electrical length ($\lambda$) of the reduced diameter lead extension 52 can be adjusted in accordance with the branch vein into which the lead system is being inserted in the desired location of the electrodes 58.

Below the electrodes 58 is the other end of the guide wire 54. Once the electrodes 58 are in the proper position and the system has been tested, the guide wire 54 is then removed. A particular advantage of the lead system 30 as shown in FIG. 2 is that no new deployment instruments or catheters are required. In other words, this system that includes the bandstop filter 38 is backwards compatible with most known deployment systems. It is also very important that the lead system 30 is designed to be extracted in the case of a broken lead, defective lead or infected lead. The lead system illustrated in FIGS. 2 and 2A, is also backwards compatible with current mechanical and laser lead extraction technologies.

Referring to FIG. 2A, one can see that there is a bandstop filter 38 and 38' associated with each of the distal electrodes 58 and 58'. Each bandstop filter consists of a capacitor C in parallel with inductor L. These combined L-C bandstop filters are placed in series with each one of the electrode lead conductors as shown. For a more complete description of bandstop filters in implanted leads, one is referred to U.S. Pat. No. 7,363,090, the contents of which are incorporated herein by reference.

Figure 3:
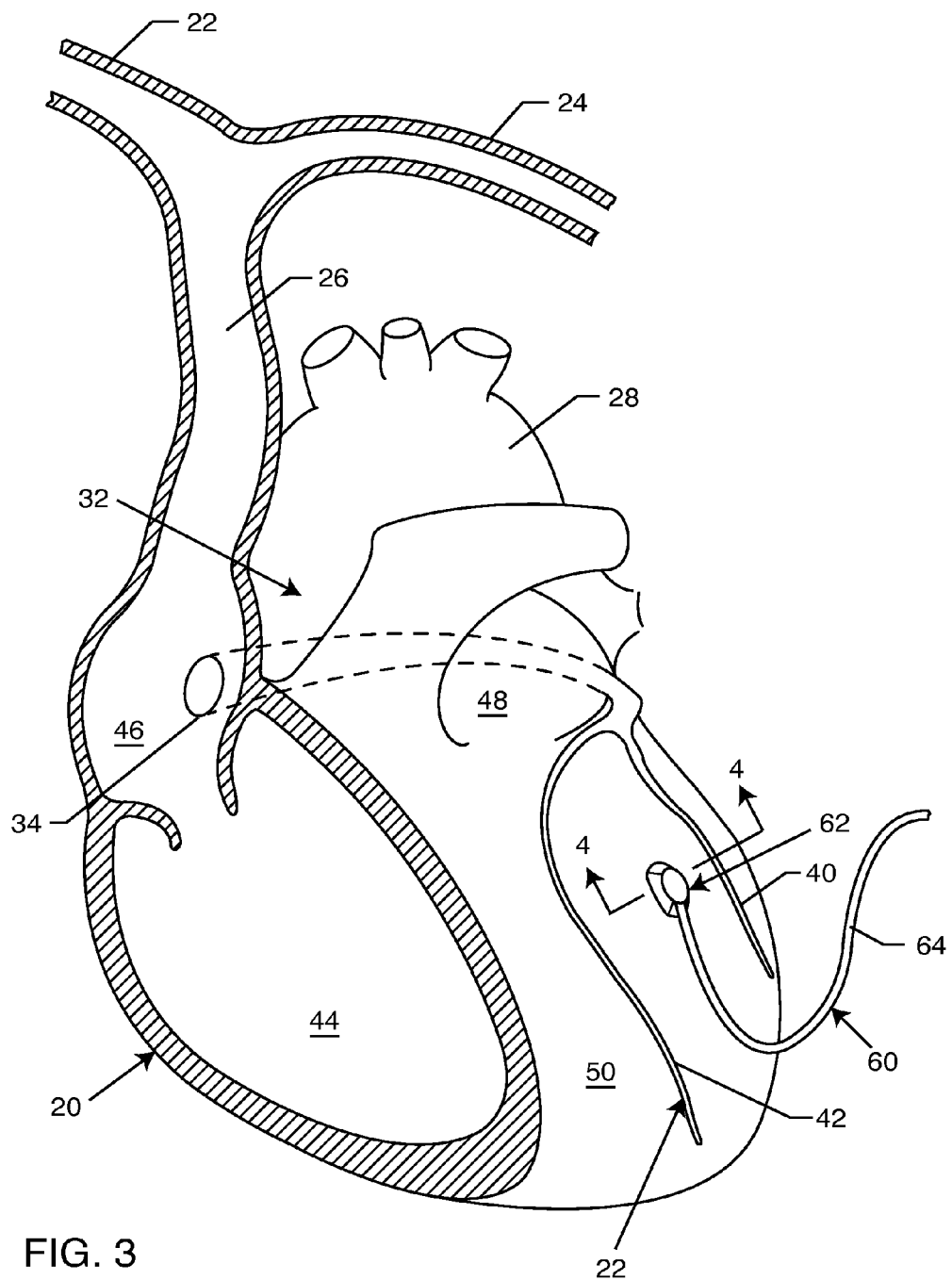
FIG. 3 is a diagrammatic representation of the human heart, showing epicardial lead attachment to the outside of the left ventricle in accordance with the present invention.

FIG. 3 is a diagrammatic representation of the human heart similar to that illustrated in FIG. 1. However, in this case, external (epicardial) electrodes 62 are attached outside and to the left ventricle 50 by means of epicardial leads 60. A sutureless myocardial lead 60, 64 is shown affixed to the outside of the left ventricle. This methodology is well known and generally involves an insertion between the ribs outside of the heart and a screwdriver type feature to affix the sutureless epicardial lead tip electrode 62 in place. Epicardial leads may also have a suture feature which can have a helical or other configuration type tip. It should be apparent that the present invention can be extended to any type of external (epicardial) electrode 62 or satellite pacer affixed to the outside of the heart, particularly outside of the left ventricle.

Figure 4:
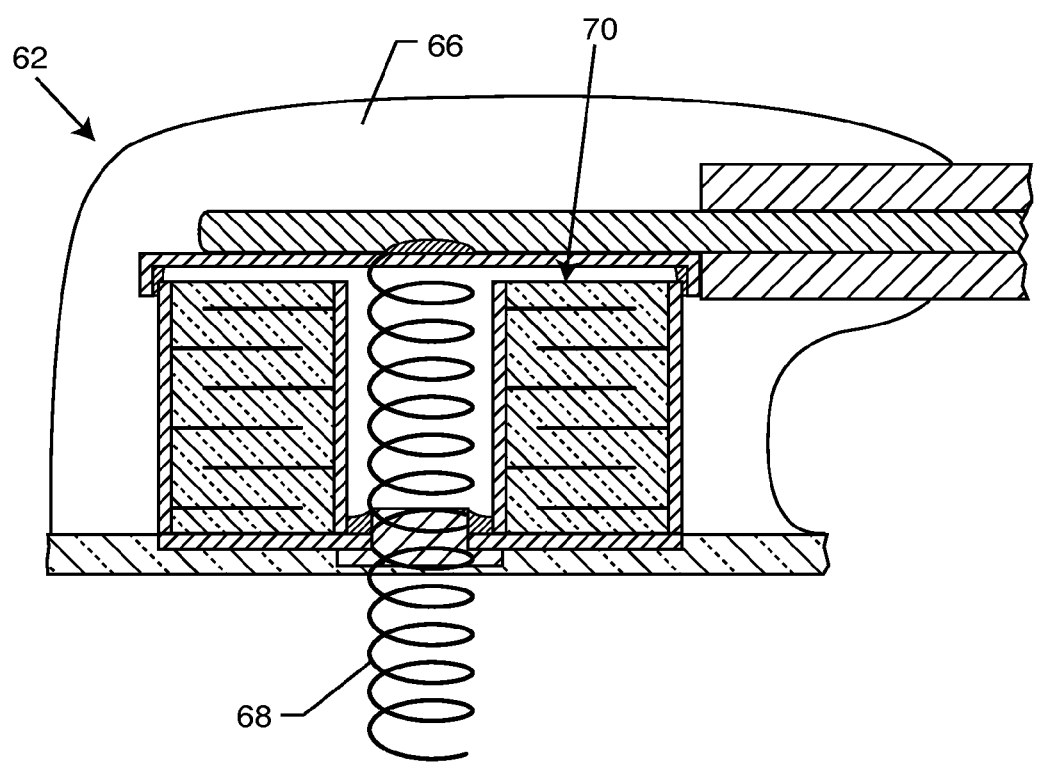
FIG. 4 is a cross-sectional view of an epicardial lead embodying the bandstop filter of the present invention taken generally along the line 4-4 in FIG. 3.

FIG. 4 is a cross-sectional view taken generally along line 4-4 of FIG. 3, illustrating an epicardial lead electrode assembly 62 which includes a bandstop filter 70. In the prior art, the epicardial lead electrode assembly 62 is typically over-molded with silicone rubber 66. The assembly shown in FIG. 4 is self-affixing to the myocardial tissue by a helical electrode structure 68. Typically this electrode is affixed into the myocardium by 3½ mechanical turns and is made of platinum-iridium alloy or equivalent biocompatible material. The helical electrode tip 68 is affixed into the myocardial tissue by a screwdriver type turning surgical tool. The bandstop filter 70, as illustrated in FIG. 4, is taken generally from FIG. 42 of US 2007/0112398 A1. It will be apparent to those skilled in the art that almost all of the other novel bandstop filter embodiments that are disclosed in US 2007/0112398 A1 and U.S. Pat. No. 7,853,325 can be incorporated into the epicardial lead 62 in FIG. 4.

Figure 5:
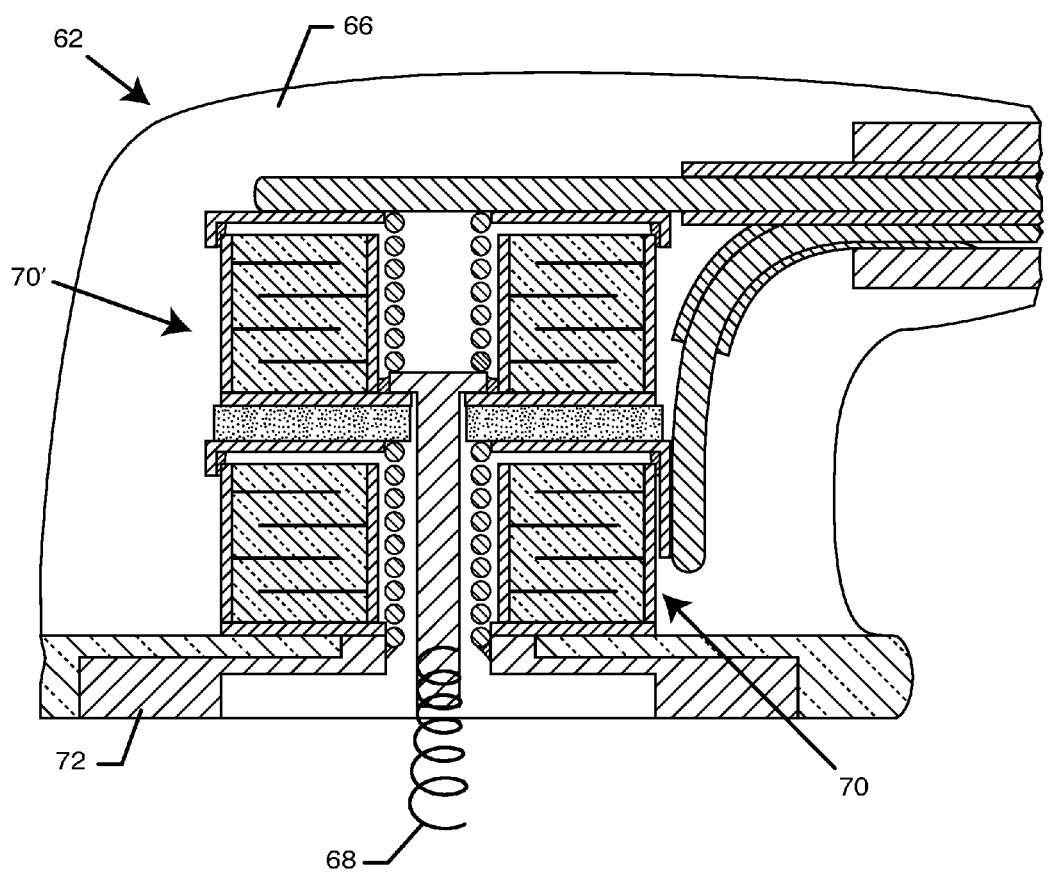
FIG. 5 is an alternative epicardial lead tip taken generally along the line 4-4 in FIG. 3.

FIG. 5 is very similar to the epicardial lead electrode assembly 62 shown in FIG. 4, except that it has a novel ring structure 72 associated with a bandstop filter chip 70. This epicardial bipolar electrode also has a bandstop filter chip 70' in series with its helical tip electrode 68. Not shown, but apparent to those skilled in the art, is that a screwdriver type head mechanism can be added for convenient adapting to prior art deployment instruments. As previously mentioned, any of the cylindrical bandstop filter chips as described in U.S. Pat. No. 7,853,325 can also readily adapted to any of the novel bandstop filter applications as described herein.

Figure 6:
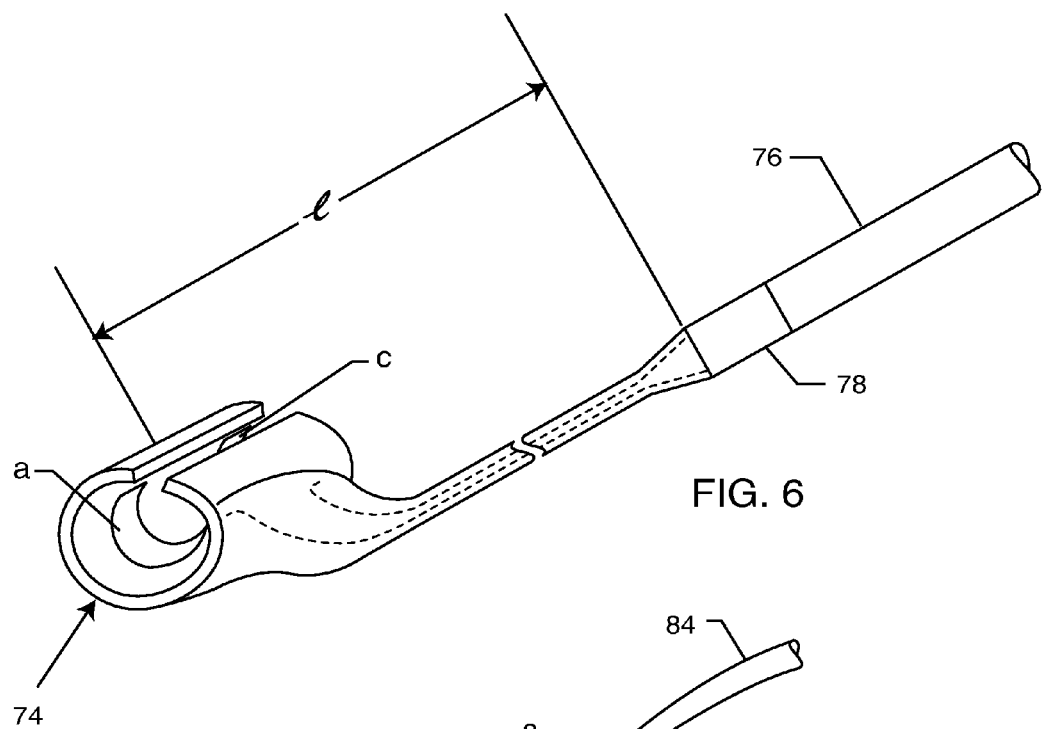
FIG. 6 illustrates a split cylinder cuff electrode designed to wrap around a nerve.

FIG. 6 illustrates a split cylinder cuff electrode 74 embodying two electrodes (Anode (a) and Cathode (c)). This is designed to be inserted by a physician around a nerve. It is a bipolar system typically consisting of a 6-8 French diameter lead body 76. A double bandstop filter chip 78 (two discrete bandstop filter chips in parallel) in accordance with the present invention is located as shown. In general, the cuff 74 is sized to match the diameter of the nerve which passes through its center. The lead body 76, after the double bandstop filter 78, is of a reduced diameter, generally in the 3-4 French range. Not shown is a closing suture which is typically used to draw the cuff together after its installed.

Figure 7:
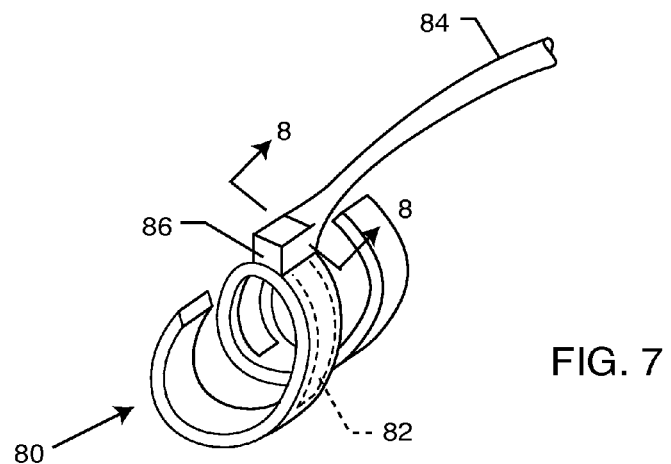
FIG. 7 illustrates a self-sizing helical cuff coil including the bandstop filter chip of the present invention.

FIG. 7 illustrates helical nerve cuffs 80 which are self-sizing. These incorporate electrode foils 82 which are well known in the prior art. The lead body 84 is attached to a bandstop filter 86 of the present invention. This can be unipolar or bipolar as shown. The electrode foil 82 can either be etched or stamped and then the termination point where the conductor attaches to the foil is either prepared or fabricated. This is the location to where the bandstop filter 86 is electrically attached and incorporated. The conductors and the foil 82 on the bandstop filter 86 are laid into a split mold and assembled and then silicone is injected into the mold. FIG. 7 illustrates one leg of a bipolar or multipolar lead. Obviously, a bandstop filter 86 would be required for each electrode foil in the multipolar configuration.

Figure 8:
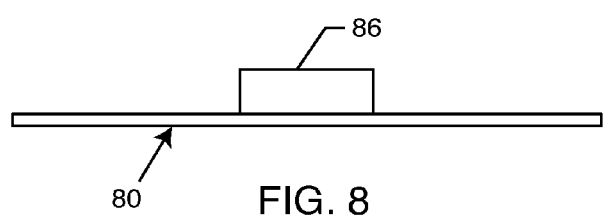
FIG. 8 is a sectional view taken generally along the line 8-8 in FIG. 7.

FIG. 8 is an enlarged sectional view taken generally along line 8-8 of FIG. 7.

Figure 9:
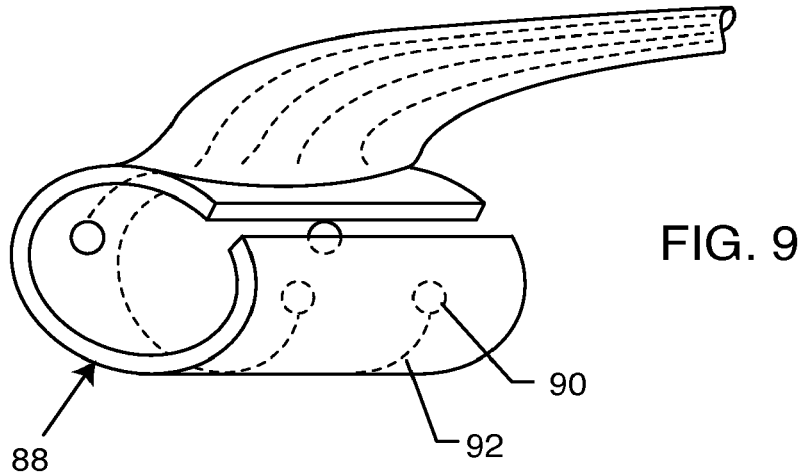
FIG. 9 illustrates a nerve cuff employing a multiplicity of electrodes and bandstop filter chips for a large nerve trunk, in accordance with the present invention.

FIG. 9 illustrates a larger multiple cuff nerve electrode 88 for current steering in a large nerve trunk. Various electrodes can be stimulated by trial and error to obtain the optimal result. For example, for pain control, one can try various electrodes and various types of electrical stimulation by trial and error until pain is minimized or eliminated. The multiple parallel filter electrodes 90, similar to that described in FIG. 4, can be placed in conjunction with each one of the conductors 92 as shown.

Figure 10:
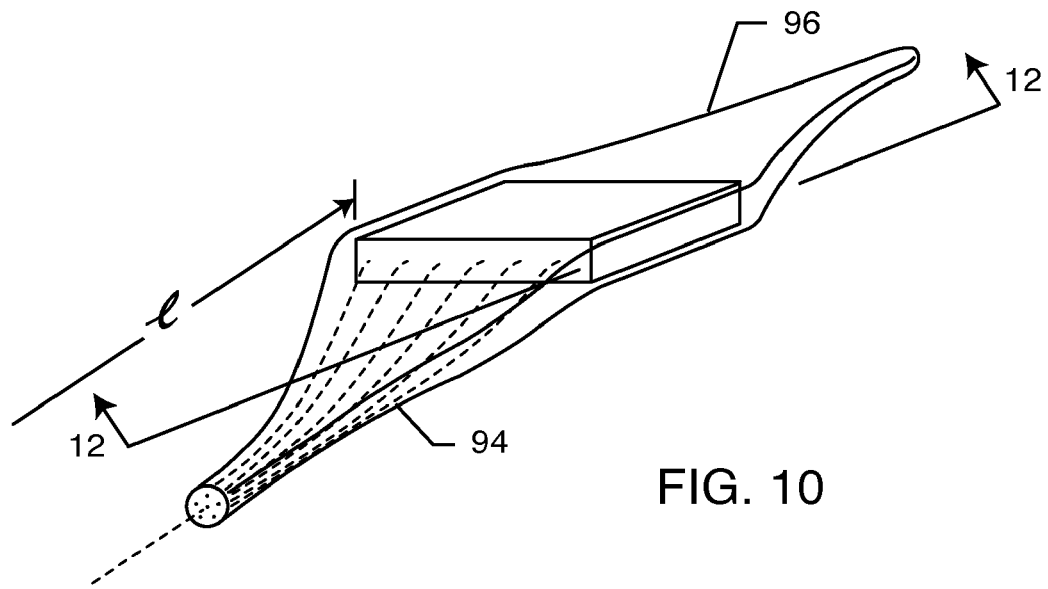
FIG. 10 illustrates one methodology of putting multiple bandstop filter chips in series with the leads of the multiple cuff electrode of FIG. 9.
Figure 11:
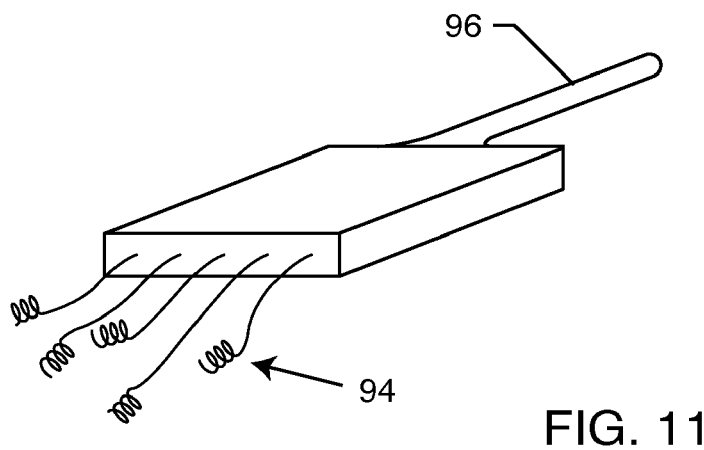
FIG. 11 illustrates a multi-conductor lead body connected to a multiple tank filter chip array that has multiple electrodes, in accordance with the present invention.

FIG. 10 illustrates an alternative in that a multiple bandstop filter array 94 is shown in series with the lead body 96. This can in turn be connected as a lead extension (beyond the bandstop filter(s)). to the cuff electrode 88 of FIG. 9 or to the multiple cuff electrodes 74, 80 illustrated in FIGS. 6 and 7. It can also be adapted to the multiple single electrodes illustrated in FIG. 11. The multiple bandstop chip as illustrated in FIGS. 10 and 11 can be made in a variety of ways utilizing the technology disclosed in US 2007/0112398 A1 and U.S. Pat. No. 7,853,325, by putting the devices on a substrate next to each other on each lead. The structure shown in FIGS. 10 and 11 can be over-molded with silicone or the like to provide reliable mechanical attachment and protection from body fluids.

Figure 12:
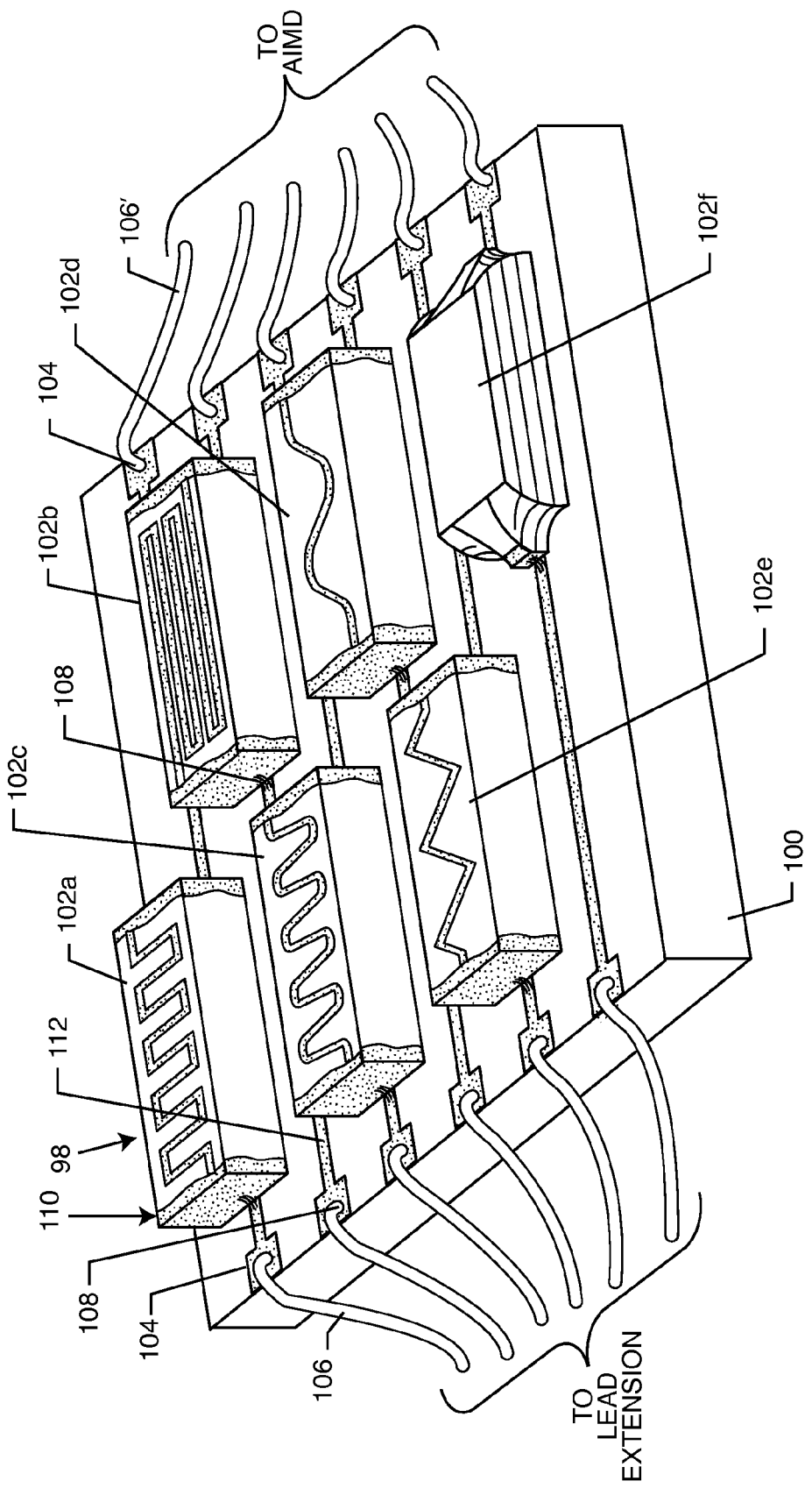
FIG. 12 is an exposed perspective view of one of many possible variations of the multiple bandstop filter array of FIG. 10.

FIG. 12 is taken generally along the line 12-12 from FIG. 10, and illustrates one of many ways to form a multiple array 98 of bandstop filter chips. One can see that there is a thin substrate 100 which can be of alumina or any other substrate material known in the prior art. Different types of bandstop filters 102a-f (MRI chips) are shown by way of illustrating that there are many ways to construct this multiple array 98. Referring to drawings from US 2007/0112398 A1 the MRI chips 102a-f are similar to FIGS. 80-85 and FIG. 136 (which is thick film deposited right on the substrate). Those skilled in the art will realize that imbedded or MEMs components can also be used to form the multiple bandstop MRI filter array 98. In addition, multilayer substrates may be used to increase packaging density. Wirebond pads 104, leads 106 and 106' and electrical connections 108 (typically laser welds or gold wirebonds), are also shown. The bandstop filter chips 102a-f have end terminations 110 as shown. There are electrical connections from these end terminations 110 to the circuit traces 112. The entire assembly is desirably over coated, over molded (with silicone or the like), or glass encapsulated to enhance mechanical strength and biocompatibility.

Figure 13:
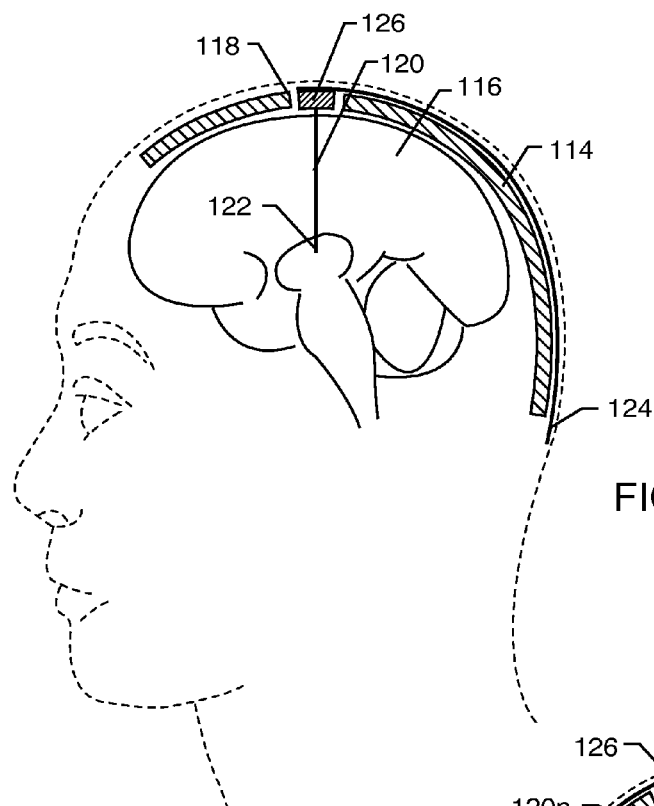
FIG. 13 is a diagrammatic, side cross-sectional view of the human head showing the placement of a deep brain probe and electrode embodying the bandstop filter of the present invention.

FIG. 13 is a diagrammatic side cross-sectional view of the human head showing the skull 114 and the brain 116. A burr hole 118 is drilled through the skull 114 for placement of deep brain probe 120 with associated electrodes 122. The deep brain probe 120 is equivalent to a lead extension in that the bandstop filter(s) is placed within burr hole container 126. This allows for the deep brain probe 120 and its associated electrodes 122 to be very small in diameter which is equivalent to the lead extension l previously discussed in FIG. 1. One can see that there is a lead 124 which has been tunneled up underneath the skin and attaches to the deep brain probe 120. The distal end of the lead 124 is generally connected to an AIMD (not shown) such as a pulse generator. The AIMD may be located somewhere in the patient's skull or tunneled through the neck and located in a pectoral implant region. One or more bandstop filters are located inside of the skull burr hole 118 in housing 126. The bandstop filter housing 126 may be located within the burr hole, above the burr hole, or even in the dural or subdural.

Figure 14:
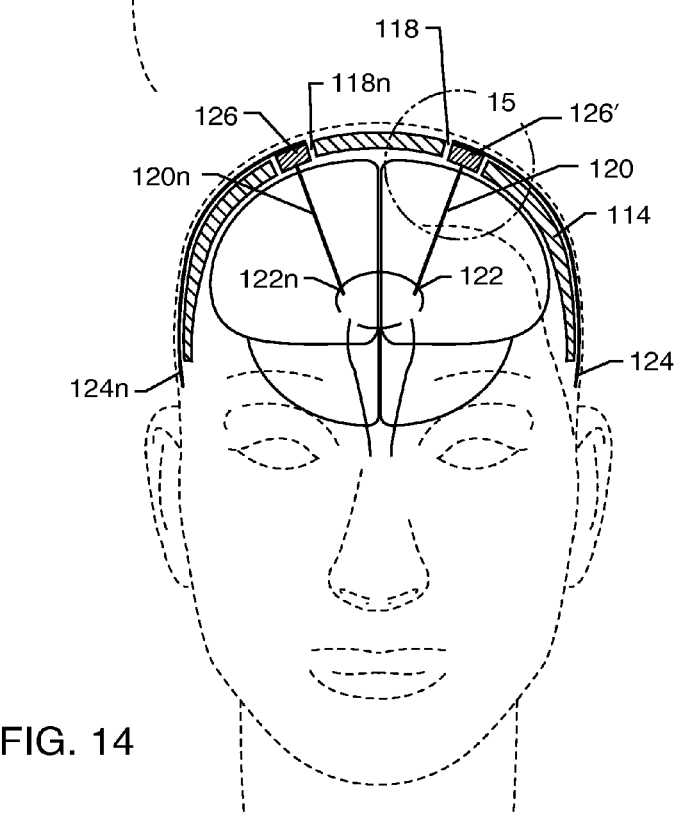
FIG. 14 is a diagrammatic, front cross-sectional view of the human head showing use of multiple deep brain probes.

FIG. 14 is a diagrammatic cross-sectional front view of the human head, showing that there can be multiple deep brain probes 120 . . . 120$_n$ placed as previously described in connection with FIG. 13. In a preferred embodiment, the top of the deep brain probe 120 and associated bandstop filters 126, 126' would be flush with the top of the skull 114. The lead 124 is generally connected to a pulse generator or transmitter which is either implanted or can sit outside the skin. There can also be a receiver which sits on the skin. The deep brain probe 120 can also have a nail head or nail shank.

Figure 15:
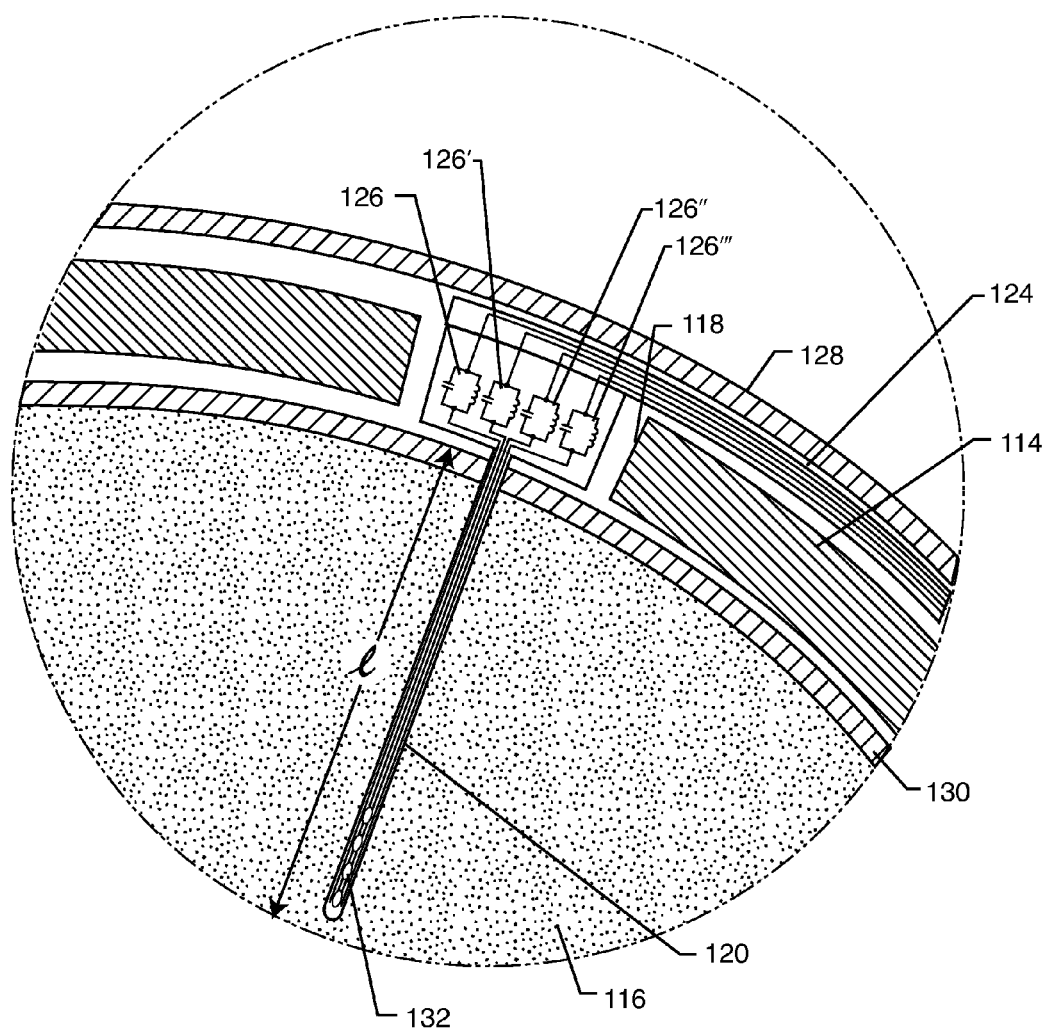
FIG. 15 is an enlarged sectional view taken generally of the area indicated by the line 15 in FIG. 14.

FIG. 15 is an enlarged sectional view of the area indicated by line 15 in FIG. 14, of the deep brain probe 120. Shown are the locations of the L-C bandstop filters 126, 126', 126'', and 126''', the skin 128 which covers the skull 114, the lead 124, the burr hole 118, dura layer 130 and the brain 116. At the end of the deep brain probe 120 are electrodes 132.

Figure 16:
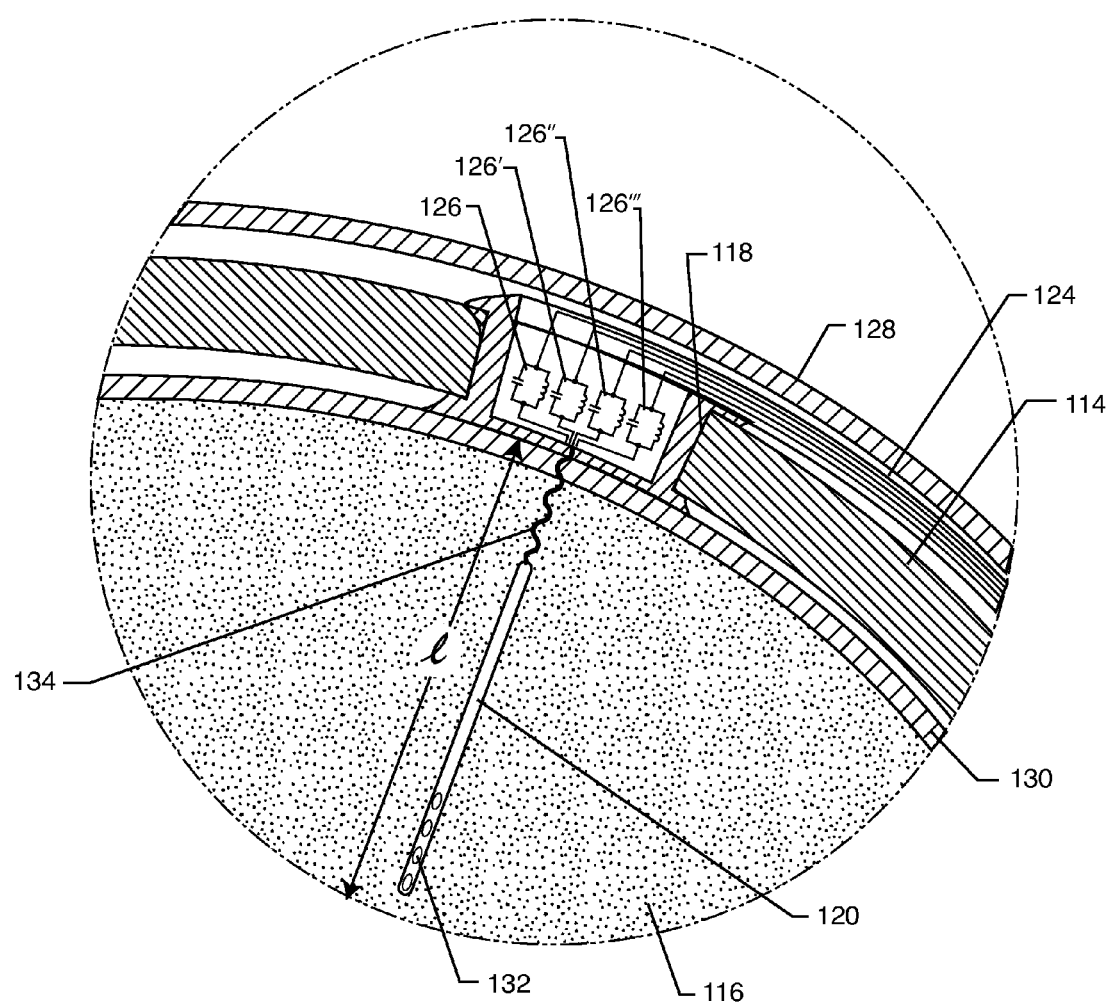
FIG. 16 is a view similar to FIG. 15, illustrating an alternative probe and electrode arrangement.

FIG. 16 illustrates an alternative view wherein a highly flexible region 134 is connected between the bandstop filter array 126 and the electrodes 132. This flexible section 134 provides strain relief for the relative motion between the skull 114 and the brain 116. One can see that the deep brain probes 120-120$_n$ form a lead extension (l) which is functionally equivalent to the lead extension 52 described previously. As noted above, the electrical length of this lead extension 120 should be less than ½ wavelength of the MRI RF pulse frequency (in body tissue), and preferably less than ¼ or ⅛ wavelength. In this particular case, since the deep brain probe 120 is implanted into thermally sensitive brain tissue, the electrical length (l) of the lead extension should be less than ⅛ wavelength.

Figure 17:
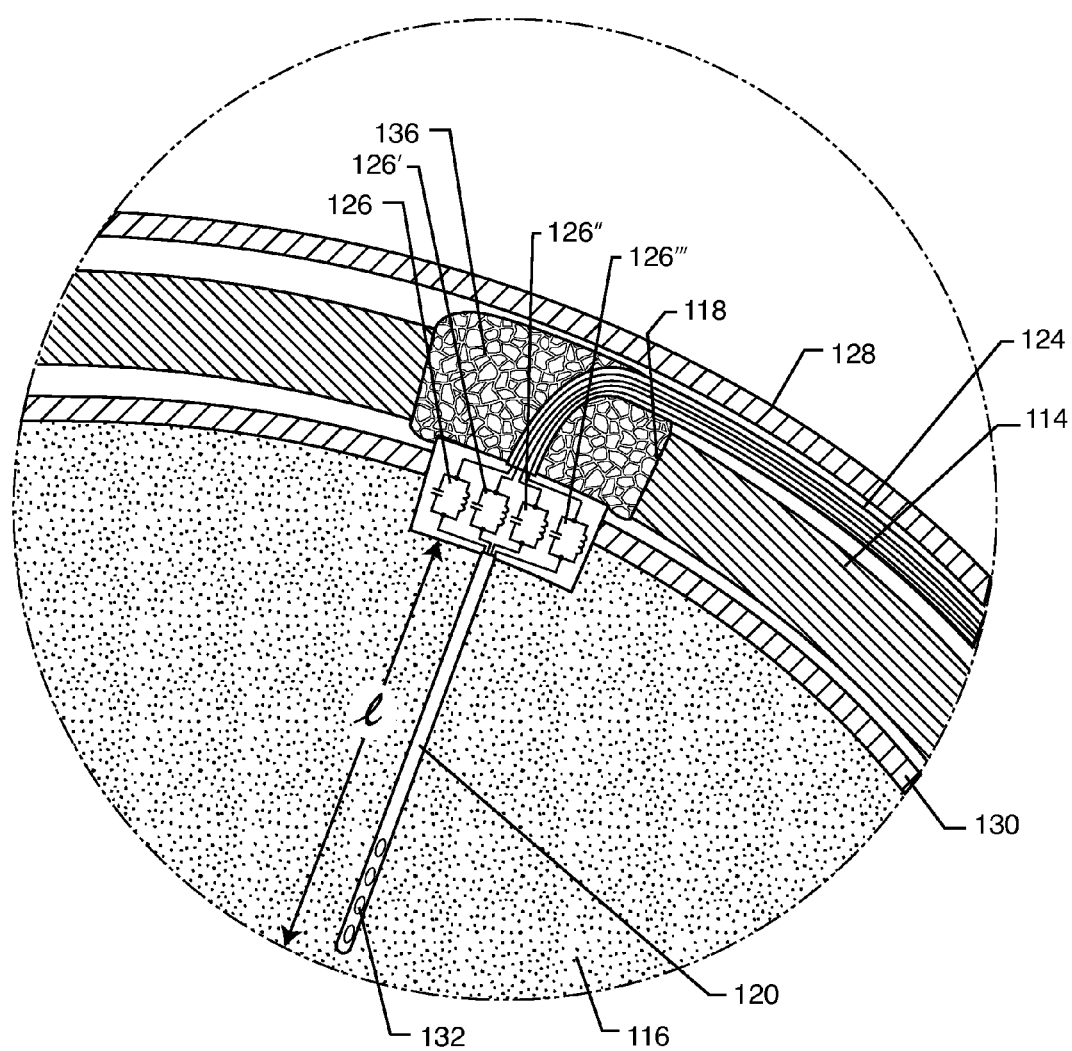
FIG. 17 is a sectional view similar to FIG. 15, except that the probe containing the bandstop filter chip is embedded under the skull and then the skull bore hole is covered with a bone encapsulant.

FIG. 17 illustrates an alternate configuration similar to FIG. 15, wherein the top of the bandstop filter array 126 is disposed below the skull 114. The burr hole 118 is covered with a bone encapsulant 136. It will be apparent to those skilled in the art that the deep brain probe 120, and its associated bandstop filter array 126, can be placed in various locations that are convenient for the physician/surgeon.

In all of the previously described embodiments, it is important that the bandstop filter be as close to the electrode-to-tissue interface as possible. The reason for this is that the lead and its associated conductors can act as an antenna (and also as a transmission line). When an antenna is an efficient multiple of a wavelength, it can pick up a great deal of energy from the external environment. In particular, the RF pulse fields from an MRI scanner can induce high levels of current in implanted leads and their associated electrodes, which can be damaging to body tissue. In general, the length of the lead extension (l), shown as element 52 in FIGS. 1 and 120 in FIGS. 15 and 16, should be as short as possible. In other words, the bandstop filter should be placed in relatively close proximity to the therapy sense or delivery electrodes as illustrated.

This principle varies with the RF pulsed frequency of the MRI machine. For example, a 0.5 Tesla machine has an RF pulsed frequency of 21 MHz In this case, the wavelength is long enough where the bandstop filter could be a considerable distance away from the delivery electrode and still be quite effective. However, when one gets up around 3 Tesla with an RF pulsed frequency of 128 MHz, then the bandstop filter must be much closer to the delivery electrode. This because the wavelength of the higher RF pulsed frequencies gets much shorter and can therefore couple more effectively to a short lead extension. In the present invention, preferably the bandstop filter is no more than 15 cm away from the delivery electrode. This will provide effective reduction in current flow at the MRI RF pulsed frequency thereby providing effective cooling at the distal electrode tips.

Figure 18:
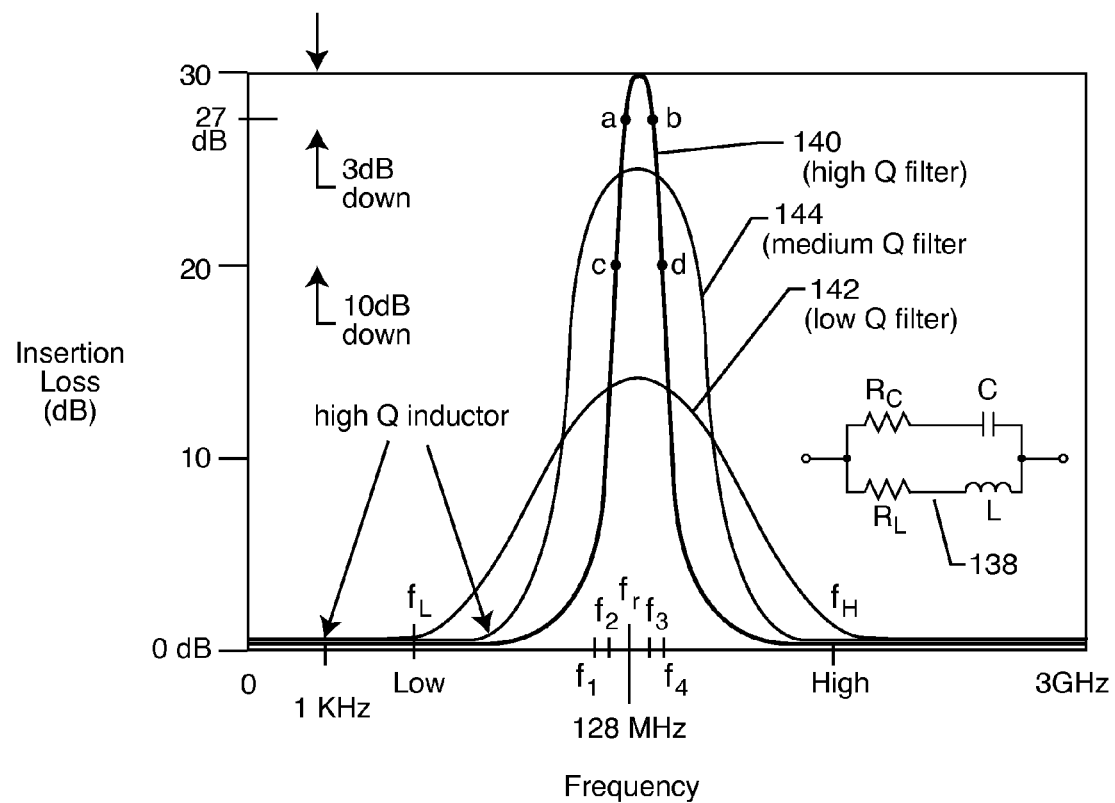
FIG. 18 is a graph of insertion loss verses frequency for bandstop filters having differing quality "Q" factors.

Referring now to FIG. 18, the efficiency of the bandstop filters (38, 70, 86, 102, 126) are also measured in terms of a quality factor, Q. The bandstop filter circuit Q is typically expressed using the following equation:

$$Q = \frac{f_r}{\Delta f_{3dB}}$$

Where $f_r$ is the resonance frequency, and $\Delta f_{3dB}$ shown as points a and b in FIG. 18 is the 3 dB bandwidth of the bandstop filter. Bandwidth is typically taken as the difference between the two measured frequencies, $f_1$ and $f_2$, at the 3 dB down points as measured on an insertion loss curve, and the resonance center frequency is the average between $f_1$ and $f_2$. As can be seen in this relationship, higher Q values result in a narrower 3 dB bandwidth. The 3 dB bandwidth is $f_2-f_1$ measured in either kHz or MHz The 10 dB down points are shown as points "c" and "d" in FIG. 18 and correspond with frequencies $f_3$ and $f_4$. Accordingly, the 10 dB bandwidth is $f_4-f_3$ measured either in kHz or MHz. In general, the insertion loss curve can also be equated to an attenuation curve wherein the source and load impedances would be 50 ohms. In a preferred embodiment, the source impedance would be the source impedance of the lead and body tissue and the load impedance would be the input impedance of the AIMD itself. Those experienced in the art will realize that the approach is equivalent.

Referring once again to FIG. 18, one can see the schematic for the bandstop filter 138 of the present invention including resistors $R_C$ and $R_L$. Resistor $R_C$ represents the equivalent series resistance of the capacitor C, or a discrete series resistor added in series with the capacitor. $R_L$ represents the equivalent series resistance of the inductor L, which is commonly due to the resistance of the wire turns or wire circuit traces of the inductor. As in the case with the capacitor, $R_L$ could also be a separate discrete chip resistor or other type of resistor added in series with the inductor portion of the bandstop filter 138. Controlling the values of these resistances controls the 3 dB bandwidths and hence the quality factor Q of the bandstop filter.

Both the 3 dB bandwidth and the 10 dB bandwidth can be varied in accordance with the application. For example, if the application is for a very specific situation, for example a dedicated MRI guided catheter lab, then only one MRI scanner is involved. For example, if it is known that only a Siemens 1.5 Tesla MRI scanner of a particular model is to be used, then we can be confident of a very specific MRI RF pulsed frequency. The bandstop filter 138 could be designed with relatively narrow 3 dB and the 10 dB bandwidths. In this case, the 10 dB bandwidth could be as small as 10 kHz. In this regard it should be borne in mind that the gradient field of the MRI scanner grades the main static field. A way to visualize this is with a patient lying in the supine position on the MRI scanner table. As the gradient field varies, the static magnetic field strength varies from head-to-toe of the patient. This means that the resonant frequency of the protons vary accordingly. In this way, the RF frequency varies thereby obtaining the image slice from the patient. About the narrowest variation is in the order of 10 kHz. On the other hand, if one were to design a bandstop filter 138 for implanted lead application where two or three MRI scanners (from different manufacturers) needed to be compatible, then a 10 dB bandwidth of 100 kHz minimum would be desirable. In general, in a particularly preferred embodiment, the 10 dB bandwidth would be on the order of megahertz, or a minimum of 500 kHz. By having a 10 dB bandwidth on the order of MHz (0.5 MHz) minimum, one can then be sure that the bandstop filter 138 would be effective over the range of commercially available or labeled 1.5 Tesla MRI scanners. Similar principles apply to 3 Tesla, 5 Tesla and other scanners that have a different static magnetic field strength. In these cases, the RF pulsed frequencies are much higher in frequency and their variation between different manufacturers and also their variation because of the gradient field can be even greater as measured in kHz.

Referring once again to FIG. 18, one can see that at very low frequencies, such as shown by $f_L$, it is important that the bandstop filter 138 represent a very low impedance. This is because the bandstop filter must pass both pacing and biologic sensing signals with very little attenuation. The same is true of very high frequencies as shown by $f_H$ although in this case it would not matter if the bandstop filter offered additional attenuation since there are no biological signals in this range.

Accordingly, the "Q" or quality factor of the bandstop circuit 138 is very important. As mentioned, it is desirable to have a very low loss circuit at low frequencies such that the biological signals not be undesirably attenuated. The quality factor Q not only determines the loss of the filter, but also affects its 3 dB and 10 dB bandwidths. If one does a plot of the filter response curve (Bode plot), the 3 dB and 10 dB bandwidths determine the attenuation curve, shape and how sharply the filter will rise and fall. With reference to curve 140 of FIG. 18, for a bandstop filter 138 that is resonate at 64 MHz, an ideal response would be one that had infinite attenuation at 64 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either. Capacitors have internal resistance known as equivalent series resistance and also have small amounts of inductance. Accordingly, the practical realization of a circuit, to accomplish the purposes of the present invention, is a challenging one. This is particularly true when one also considers that the bandstop circuit must also be miniature, highly reliable, and completely biocompatible.

The performance of the circuit is directly related to the efficiency of both the inductor L and the capacitor C; the less efficient each component is, the more heat loss that results, and this can be expressed by the addition of resistor elements, $R_C$ and $R_L$ to the ideal circuit diagram. The effect of lower Q in the bandstop circuit 138 is to broaden the resonance peak about the resonance frequency. By deliberately using a low Q capacitor and/or inductor, one can broaden the resonance such that a moderately high impedance (attenuation) is presented at multiple MRI RF frequencies.

Referring again to FIG. 18, one can control both the 3 dB bandwidth and the 10 dB bandwidth by controlling the amount of resistance $R_C$ and $R_L$ in the bandpass filter circuit 138. One must be careful not to let the resistance in series with the inductor be too large or biological frequencies will be attenuated. The reason for this is that at very low frequencies (below 1 kHz), the inductive reactance tends to be very low (approximate zero). At the same time, at very low frequencies the capacitive reactance tends to look infinite. Accordingly, for proper operation of delivering pacing pulses or sensing biological activity, the resistor value $R_C$ really does not matter much. Accordingly, a good way to control the Q of the bandstop filter 138 is to establish resistance $R_L$ that is consistent with the parasitic resistances of inductor windings or turns and also carefully control the capacitor Q. Another reason that one must control the resistive loss $R_L$ of the inductor L is that if the resistance gets too high, excessive heating of the bandstop filter could occur. This is because there is a high frequency current that oscillates at the MRI pulsed frequency between the capacitor's C electric field and the inductor's L magnetic field. This circulating current can create heating about the bandstop filter in one of two ways: 1) by $I^2R$ heating in either resistance $R_L$ or $R_C$ (or both), or by eddy current losses in the hermetic or shield housing that surrounds the bandstop filter. Accordingly, a careful balance between component design and bandstop filter Q must be achieved.

The Lamour equation tells us that the frequency of the pulsed RF field is equal to the MRI constant times the static magnetic field strength of the clinical scanner in Teslas. This frequency is approximately 64 MHz for a typical prior art 1.5-Tesla hydrogen scanner. However, not all marketing labeled 1.5-Tesla scanners are the same. There is considerable variation in the static magnetic field strength from different manufacturers. This results in several hundreds of kilohertz or even a half megahertz of difference between the RF pulsed frequency between the various scanner manufacturers. Accordingly, the bandstop filter 138 is designed to be resonant at a center frequency, $f_r$, representing the center of a range of RF pulsed frequencies. As shown in FIG. 18, a resistance element $R_C$, $R_L$ or both, is added in order to increase the 3 dB bandwidth of the L-C trap filter 138. Referring once again to FIG. 18, one can see the attenuation curve for a high Q filter 140, a medium Q filter 144, and a low Q filter 142. The medium Q filter would work for many applications, but the attenuation of the low Q filter generally would not be adequate to be sure that excessive heating at a distal electrode would not occur. In the present invention, the desired curve shapes are 140 or 144. To put this in perspective, for an ideal bandstop filter (meaning that $R_C$ and $R_L$ are both zero), the filter response curve would look like a straight up and down line (not shown) centered above $f_r$. This would, of course, be so narrow that it would be both impractical (other than at cryogenic temperatures) to build and impractical for use over a range of MRI scanners. This resistance element can be a discrete resistor or it can be formed from the leads or circuit traces as a parasitic element that forms the inductance L itself. For simplicity, this resistance element is not shown in FIG. 16 and the subsequent drawings. However, it will be understood that the bandstop filter is designed to attenuate over a range of MRI RF pulsed frequencies on the order of tens of kilohertz, hundreds of kilohertz, or even megahertz.

Figure 19:
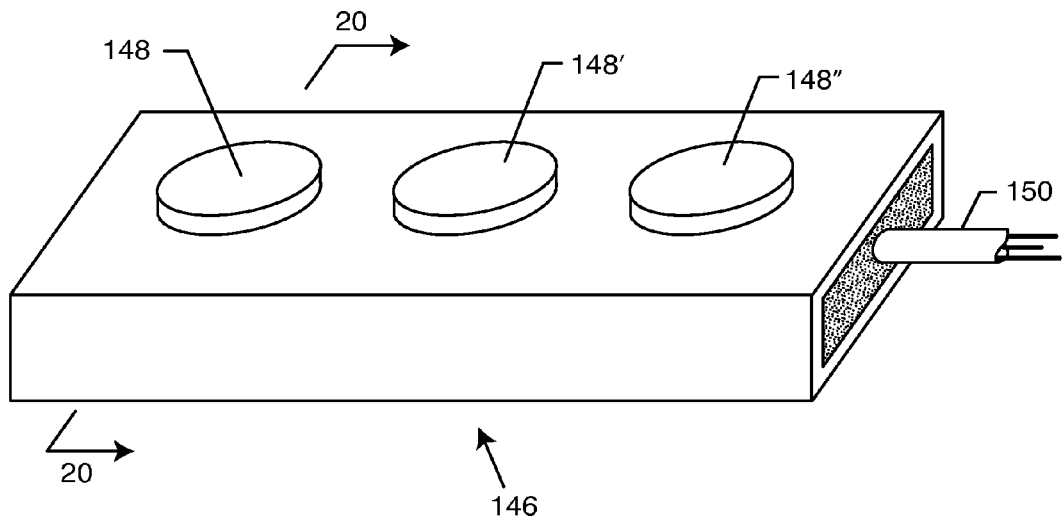
FIG. 19 is a perspective view of a distal electrode PAD applicable to a wide variety of neurostimulator applications.

FIG. 19 illustrates a distal PAD electrode 146 applicable to a wide variety of neurostimulator applications. Neurostimulators include cochlear implants, deep brain stimulators, spinal cord stimulators, incontinence stimulators, general pain control stimulators, vagus nerve stimulators, Parkinson's tremor control stimulators and the like. Typical prior art stimulators often come with a variety of PAD electrodes such as that shown in FIG. 19. Three neurostimulation electrodes 148, 148' and 148" are shown, however, these can vary anywhere from one, ten or even twenty-four or more neurostimulation electrodes. For example, in cochlear neurostimulators, there are commonly sixteen conductors, which are routed to a bundle of sixteen electrodes to make contact to the auditory nerves. Referring back to FIG. 19, one can see that there is a lead body 150 which contains three conductors that are connected to an external or implanted active medical device (not shown).

Figure 20:
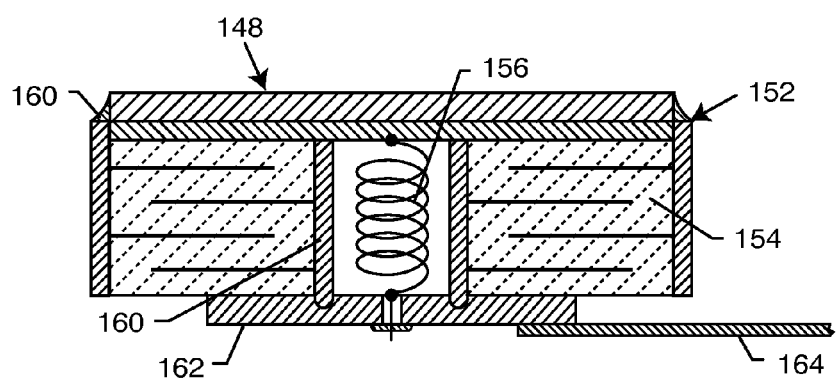
FIG. 20 is a sectional view taken generally along the line 130-130 of FIG. 19.

FIG. 20 is a cross-sectional view taken generally along line 20-20 of FIG. 19, and illustrates one form of the novel inductor capacitor bandstop filter 152 of the present invention. One can see that there is a discoidal feedthrough capacitor 154 with an air core inductor 156 running through its center. These concepts were previously described in connection with FIGS. 45 and 47 of US 2007/0112398 A1. In this case, the distal PAD electrode 148 has a laser weld or equivalent biocompatible electrical attachment 160 to the surrounding metallization of the capacitor 154. There is also another conductive plate 162 shown connected to the inductor 156 on the opposite side. Lead 164 is in turn mechanically and electrically connected to this plate 162. Lead 164 is then routed through the flexible neurostimulator PAD electrode 146 as shown in FIG. 19. Lead 164 becomes part of the lead body 150 which would be routed to the AIMD.

Figure 21:
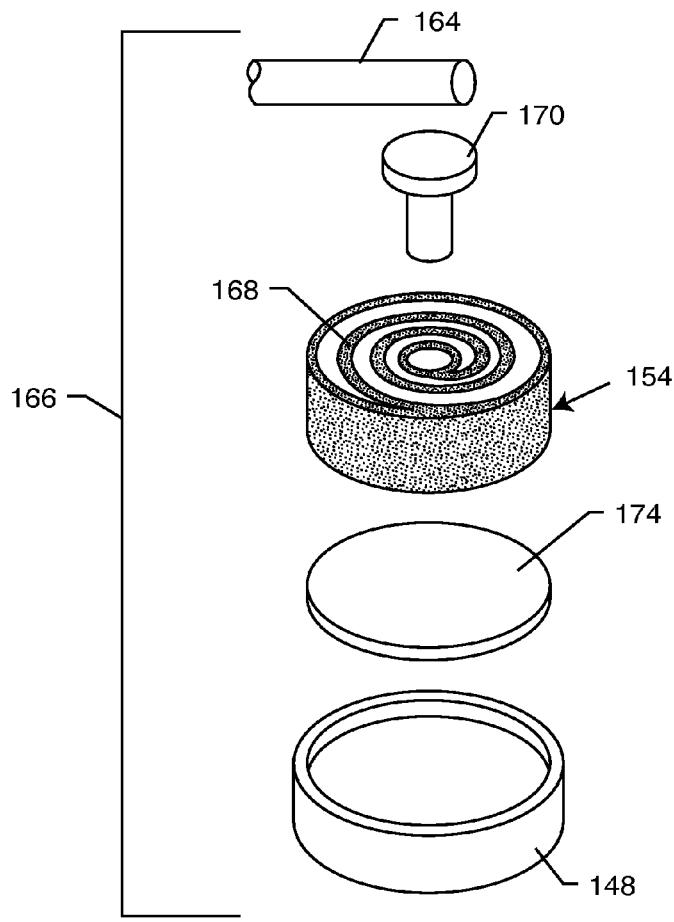
FIG. 21 is an exploded perspective view of an alternative structure accomplishing the same filtering result as the structure shown in FIGS. 19 and 20.
Figure 22:
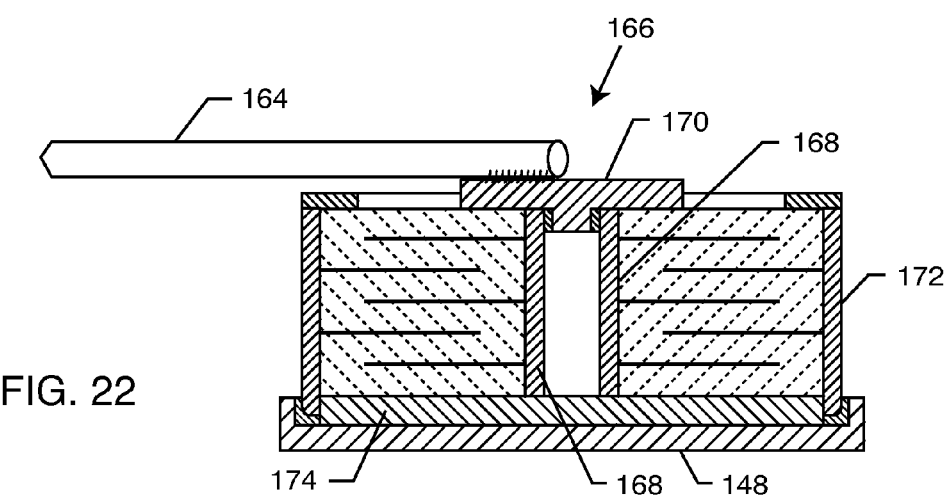
FIG. 22 is a vertical sectional view of the components illustrated in FIG. 21, in their assembled configuration.

FIGS. 21 and 22 show alternative ways of accomplishing the same thing using a feedthrough capacitor structure as described in FIGS. 115 and 118 US 2007/0112398 A1 in the PAD electrode 166 of FIG. 20. In this case, the inductor 168 has been printed onto the top of the capacitor 154 or attached to the capacitor by means of a supplemental substrate. Lead 164 is connected to the capacitor's internal diameter metallization 168 as shown using an intermediate contact plate 170. The PAD electrode 148 is electrically and mechanically attached to the capacitor outside diameter metallization 172, but electrically insulated from the internal metallization 168, such as with an insulative layer or liner 174. This is shown inverted for simplicity as compared to FIG. 19.

Figure 23:
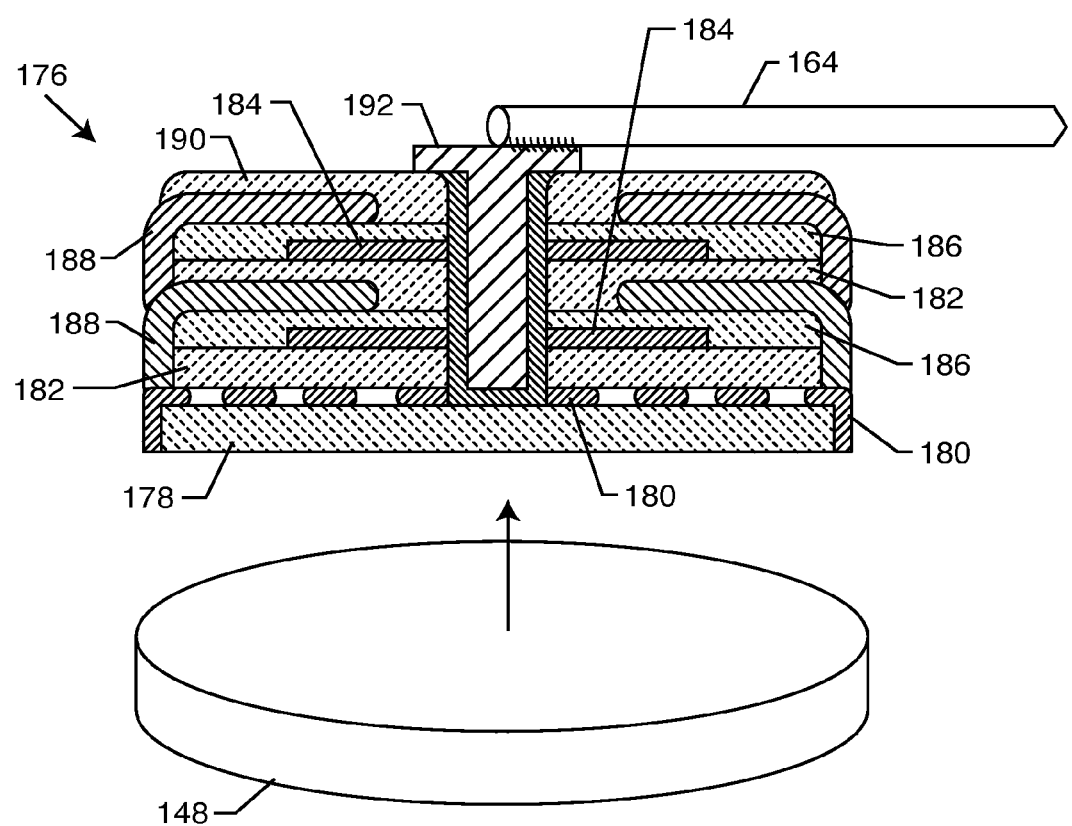
FIG. 23 is a sectional view similar to FIG. 22, illustrating another alternative for building up the novel parallel inductor bandstop filter for neurostimulator applications.
Figure 24:
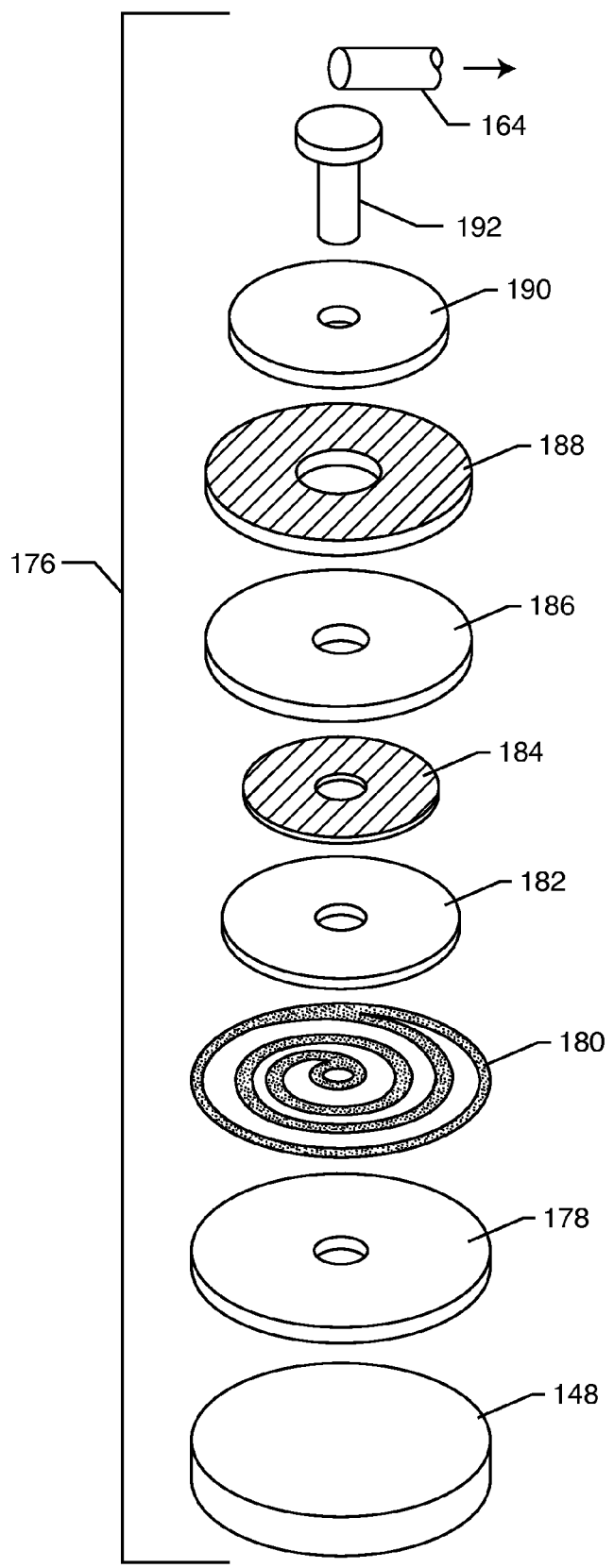
FIG. 24 is an exploded perspective view of the components of the structure shown in FIG. 23.

FIG. 23 illustrates another alternative using thick film techniques to build up in layers a parallel inductor bandstop filter for neurostimulator applications as previously shown in FIG. 19. Again, this electrode assembly 176 is shown inverted for simplicity. The distal PAD electrode 148 forms a substrate such as used for thick film deposition of various capacitor and inductor layers. The structure 176 of FIG. 23 is better understood by looking at the exploded view in FIG. 24. Starting at the bottom we have the distal PAD electrode 148 for neurostimulator applications. An insulative layer 178 is first imprinted on this conductive electrode 148 and then one or more inductor layers 180 are imprinted thereon. Then another insulative layer 182 is laid on top of the inductor layer 180. Onto this a capacitor inner diameter electrode 184 is printed. Then another insulative layer 186 is printed. Then an outside diameter capacitor electrode 188 is imprinted. Many alternating layers of electrodes 184 and 188 can be stacked up as desired to achieve the required capacitance value. Then an overall insulative layer 190 is laid down. As is well known in conventional thick film or tape manufacturing processes, there is usually a drying step between each one of these operations. The entire structure is then sintered at high temperature to form a rugged monolithic structure. An electrical contact 192 is then inserted using a suitable electrical connection material to make contact with both the inside diameter of the inductor 180 and the inside diameter of the inner diameter capacitor electrode plate stack 184. In turn, neurostimulator lead 164 is electrically connected to this contact insert 192. The outside diameter of the inductor makes contact with neurostimulator electrode PAD 148. The capacitor's ground electrode plates 188 also make electrical contact with the distal electrode PAD 148. This has the effect of putting the capacitance in parallel with the inductance.

Figure 25:
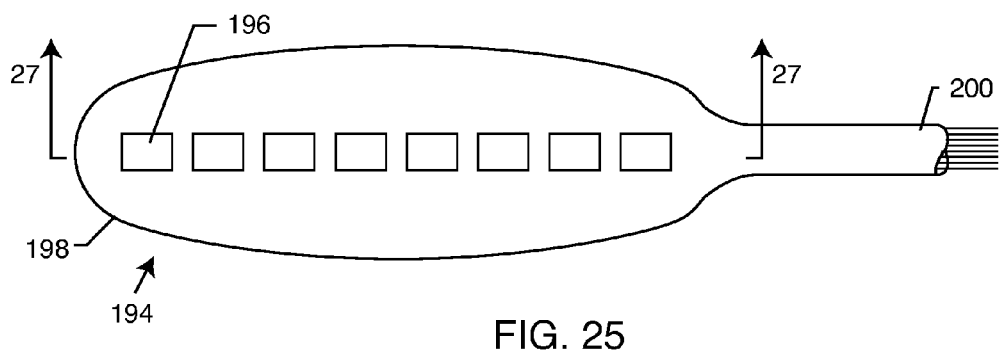
FIG. 25 is a fragmented top plan view of an exemplary paddle or PAD electrode embodying the present invention.

FIG. 25 illustrates a paddle or PAD electrode array 194 which could be used, for example, in spinal cord simulator applications. It has eight electrodes 196 housed in a biocompatible insulative and flexible body 198. An eight conductor lead 200 (there can be any number) is connected respectively to each of the eight electrodes 196. As previously discussed, the elongated lead 200 can pick up significant amounts of RF energy during MRI scanning. It is very important that the electrodes 196 do not overheat since they are in direct contact with body tissue, for example, with the spinal cord.

Figure 26:
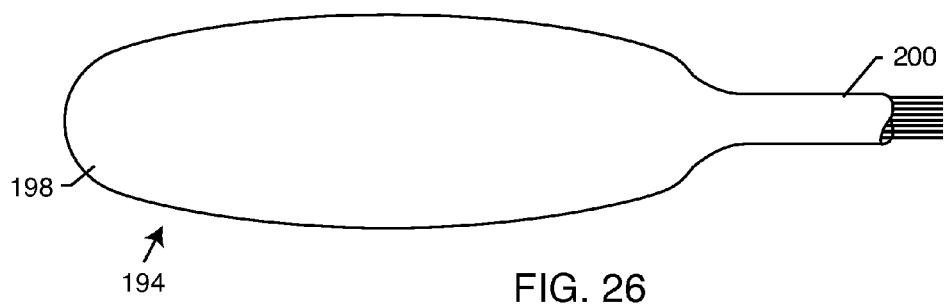
FIG. 26 is a bottom plan view of the paddle or PAD electrode shown in FIG. 25.

FIG. 26 illustrates the reverse side of the paddle electrode 194.

Figure 27:
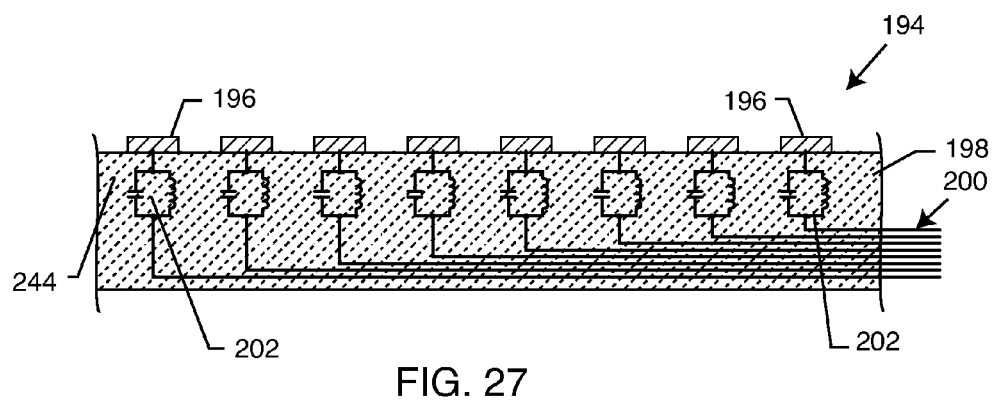
FIG. 27 is an enlarged sectional view taken generally along the line 27-27 in FIG. 25.

FIG. 27 is a sectional view taken of section 27-27 from FIG. 25. Shown are the eight electrode PADs 196 each of which is connected in series with a bandstop filter 202 of the present invention. Accordingly, there are eight electrode PADs 196 in contact with body tissue, there are eight bandstop filters 202 and eight conductors that make up the lead bundle 200. Referring once again to FIG. 27, if it were necessary to save space, the bandstop filters 202 could be placed at a point proximal from the electrode PAD array. The electrodes would then be located at the distal end of a lead extension in accordance with the present invention. One example would be as illustrated in FIG. 12 where the bandstop filters were placed on a substrate proximal to the electrode PAD array. By placing the bandstop filters at the proximal end of such a lead extension, it is then possible to make both the lead body 200 and the associated electrode housing 194 much smaller.

Figure 28:
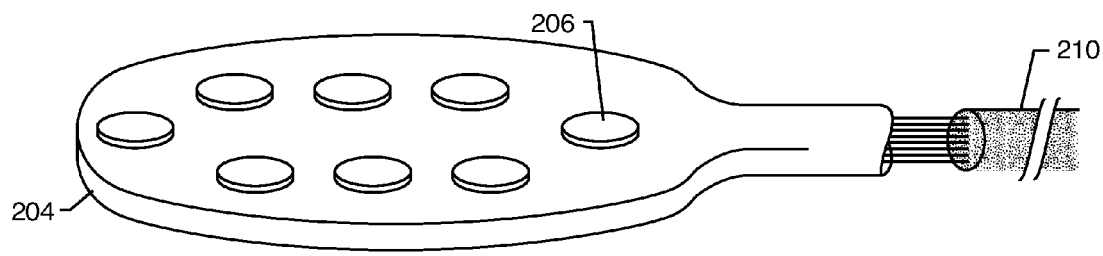
FIG. 28 illustrates the distal end of a typical neurostimulator paddle electrode.
Figure 30:
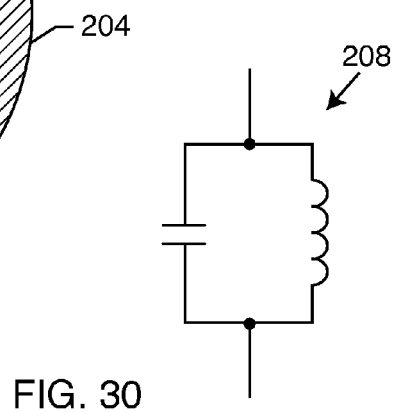
FIG. 30 is an electrical schematic illustration of the bandstop filters found in the paddle electrodes of FIGS. 25-29.

FIG. 28 illustrates the distal end of a typical neurostimulator paddle electrode 204, which in this case has eight electrode contact points 206. In this case, each of these eight electrodes 206 would have in series with it a bandstop filter 208 as shown in FIG. 30.

Figure 29:
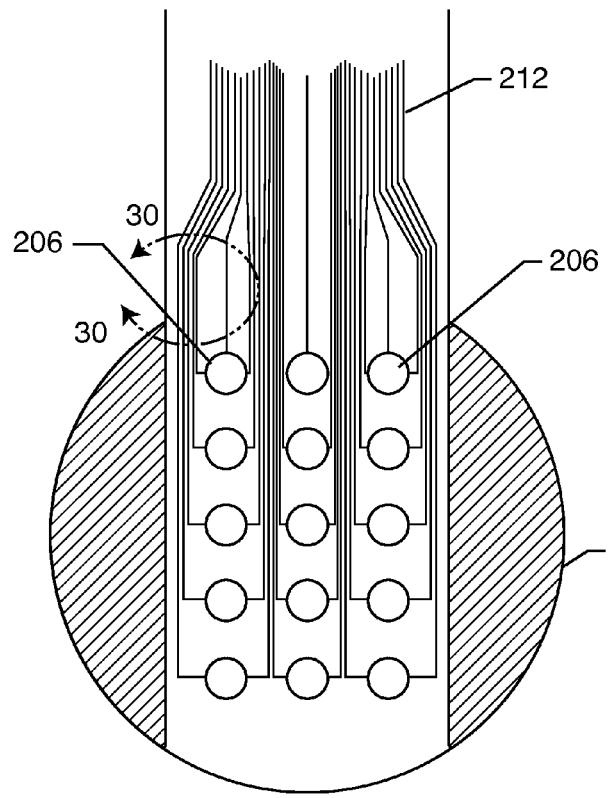
FIG. 29 is similar to FIG. 28, except that the paddle lead has been replaced with a series of flex cable electrodes.

FIG. 29 is similar to FIG. 28 except the paddle lead 210 (FIG. 28) has been replaced with a series of flex cable electrode conductors 212. Again, each of the electrodes 206 has in series with it a bandstop filter 208.

Figure 31:
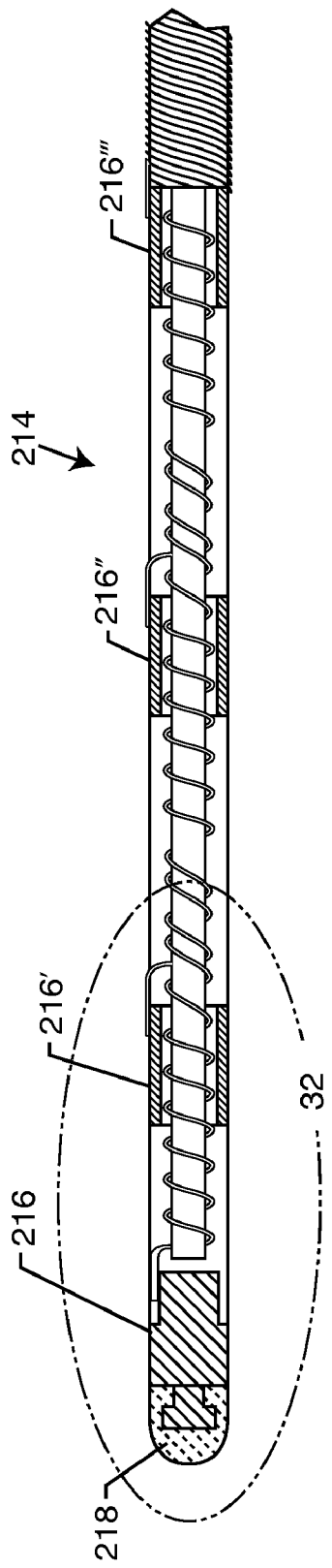
FIG. 31 is a fragmented sectional view of a prior art neurostimulation electrode probe.

FIG. 31 illustrates a prior art neurostimulation electrode probe 214 or a common ablation probe or a catheter. As one can see, there are a multiplicity of stimulation electrodes 216-216'''. In this particular application the end tip 218 is insulative.

Figure 32:
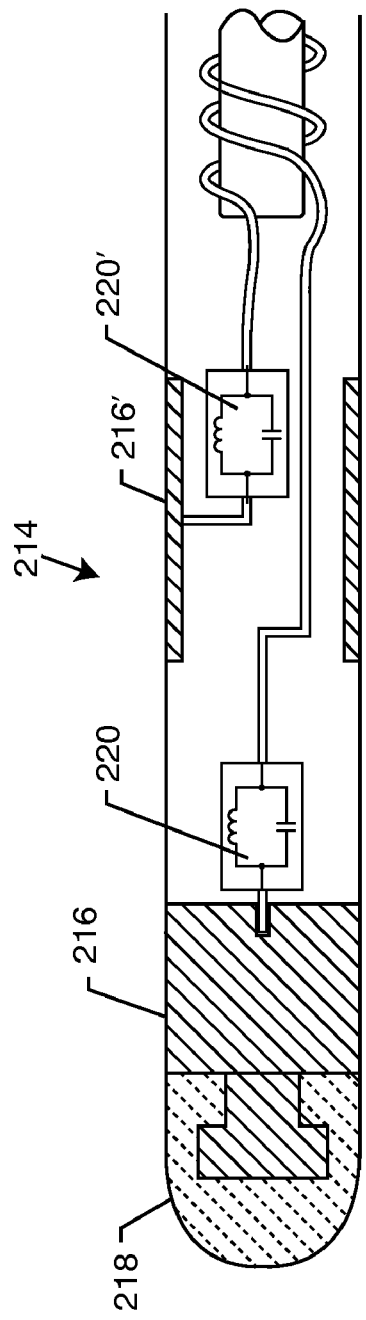
FIG. 32 is an enlarged sectional view of the area 32 in FIG. 31, illustrating modifications to the prior art structure to incorporate the novel bandstop filters of the present invention.

FIG. 32 is the probe 214, neurostimulation tip 218, ablation probe or catheter of FIG. 31, modified to include novel bandstop filters 220 and 220' of the present invention. One can see that these are placed in conjunction with the stimulation electrodes 216, 216' and so on. As many as desired can be stacked as shown. This has the effect of placing the bandstop filter 220 of the present invention in series with each one of the stimulation rings 216 and thereby limiting/preventing the flow of MRI induced RF currents. A common application for the type of electrode probe arrangement shown in FIG. 31 would be a cochlear implant wherein there would be sixteen ring electrodes 216. FIG. 31 illustrates the prior art and FIG. 32 illustrates the principles of the present invention wherein a bandstop filter BSF has been placed in series with each of the electrodes 216. The probe or catheter of FIG. 32 could also be configured as a lead extension as previously described. In other words, the bandstop filters 220, 220' and so on could be located at the proximal end of the lead extension. This would allow the probe and its associated electrodes to be smaller in diameter for specific physiological applications.

From the foregoing, it will be appreciated that the medical lead systems illustrated and described may be advantageously used in a number of environments, with different types of active implantable medical devices (AIMDs) and with different types of MRI equipment. Moreover, a precise construction and configuration of the bandstop filters utilized with the lead systems may have a wide variety of configurations and applications as illustrated in U.S. Pat. No. 7,363,090; U.S. Pat. No. 7,853,324; U.S. Pat. No. 7,702,387; U.S. Pat. No. 7,853,325; US 2007/0112398 A1; US 2008/0195180 A1; US 2008/0049376 A1; US 2008/0132987 A1; US 2008/0269591 A1; US 2010/0100164 A1; US 2010/0198312 A1; US 2010/0280584 A1; and U.S. Ser. Nos. 12/873,862; and 12/891,292.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A medical lead system, comprising: a.)
an implantable lead comprising at least one electrical conductor having a first length extending to a proximal lead end and a distal lead end; b.)
an electrode located at the distal lead end, the electrode being contactable with biological cells; and c.)
at least one bandstop filter comprising a capacitor in parallel with an inductor, the parallel capacitor and inductor being in series with the electrical conductor, wherein the bandstop filter has a Q wherein the resultant 3 dB bandwidth is at least 10 KHz.

2. The medical lead of claim 1, wherein the lead comprises an epicardial lead, a split-cylinder cuff electrode, a self-sizing nerve cuff, a multiple-cuff nerve electrode, a multiple bandstop filter array, a deep brain electrode, a paddle electrode, a PAD electrode, a ring electrode, an active fixation tip electrode, a passive fixation tip electrode, a lead extension electrode, a probe, a catheter, or an ablation probe.

3. The medical lead of claim 2, wherein the multiple bandstop filter array comprises a plurality of bandstop filters disposed on a substrate at spaced location along the implanted lead, or in a PAD or paddle electrode array.

4. The medical lead of claim 3, wherein at least one of the bandstop filters comprises a bandstop filter chip.

5. The medical lead of claim 3, wherein at least one of the bandstop filters is thick-film deposited onto the substrate.

6. The medical lead of claim 2, wherein the ring electrode comprises a cochlear electrode.

7. The medical lead of claim 1, including a flexible conductor disposed between the bandstop filter and the electrode.

8. The medical lead of any of claims 1-6, wherein the bandstop filter is disposed within or adjacent to the electrode.

9. The medical lead of claim 1, wherein the 3 dB bandwidth of the bandstop filter spans a plurality of MRI RF pulsed frequencies.

10. The medical lead of claim 1, wherein the lead comprises a proximal section and distal reduced-diameter lead extension, and wherein the bandstop filter is disposed at or near the proximal end of the lead extension.

11. The medical lead of claim 10, wherein a second length of the lead extension is less than ½ of an electrical wavelength of a selected center frequency of the 3 dB bandwidth.

12. The medical lead of claim 11, wherein a second length of the lead extension is less than ¼ of an electrical wavelength of a selected center frequency of the 3 dB bandwidth.

13. The medical lead of claim 12, wherein a second length of the lead extension is less than ⅛ of an electrical wavelength of a selected center frequency of the 3 dB bandwidth.

14. The medical lead of claim 1, wherein the bandstop filter includes fixation tines.

15. The medical lead of claim 1, wherein the bandstop filter is no more than 15 cm away from the electrode.

16. The medical lead of any of claims 1-6, or 9-15, wherein the Q of the bandstop filter provides a 10 dB bandwidth that is at least 10 kHz.

17. The medical lead of claim 16, wherein the Q of the bandstop filter provides a 10 dB bandwidth that is at least 100 kHz.

18. The medical lead of claim 17, wherein the Q of the bandstop filter provides a 10 dB bandwidth that is at least 0.5 MHz.

19. The medical lead of claim 1, wherein the bandstop filter comprises a capacitance in parallel with an inductance, said parallel capacitance and inductance being in series with the lead wherein the bandstop filter is resonant at a selected center frequency.

20. The medical lead of claim 19, wherein the capacitance comprises a discrete capacitor.

21. The medical lead of claim 19, wherein the inductance comprises a discrete inductor.

* * * * *

UNITED STATES PATENT AND TRADEMARK OFFICE
CERTIFICATE OF CORRECTION

PATENT NO.        : 8,155,760 B2
APPLICATION NO.   : 13/026949
DATED             : April 10, 2012
INVENTOR(S)       : Randy Westlund et al.

It is certified that error appears in the above-identified patent and that said Letters Patent is hereby corrected as shown below:

Column 15, line 32 - delete "system"

Column 16, line 1 - delete "location" and insert -- locations --

Column 16, line 17 - "section and distal" should be "section and a distal"

Signed and Sealed this
Fifth Day of June, 2012

David J. Kappos
*Director of the United States Patent and Trademark Office*